(12) United States Patent
Efrat et al.

(10) Patent No.: US 11,511,031 B2
(45) Date of Patent: Nov. 29, 2022

(54) LIPOASPIRATE PROCESSING

(71) Applicant: Alma Lasers Ltd., Caesarea (IL)

(72) Inventors: Alon Efrat, Caesarea (IL); Meital Grafi-Cohen, Caesarea (IL); Hanit Brenner-Lavie, Caesarea (IL)

(73) Assignee: Alma Lasers Ltd.

( * ) Notice: Subject to any disclaimer, the term of this patent is extended or adjusted under 35 U.S.C. 154(b) by 0 days.

(21) Appl. No.: 17/549,127

(22) Filed: Dec. 13, 2021

(65) Prior Publication Data

US 2022/0096729 A1 Mar. 31, 2022

Related U.S. Application Data

(63) Continuation of application No. PCT/IB2021/051910, filed on Mar. 8, 2021.

(60) Provisional application No. 62/986,806, filed on Mar. 9, 2020.

(30) Foreign Application Priority Data

May 28, 2020 (GB) ..................................... 2008023

(51) Int. Cl.
*A61M 1/00* (2006.01)
(52) U.S. Cl.
CPC .................................. *A61M 1/892* (2021.05)
(58) Field of Classification Search
CPC ... A61K 35/35; A61M 1/0001; A61M 1/3692; A61M 1/3693; A61M 2202/0437; A61M 2202/08; A61M 2205/75; C12M 45/02; C12M 45/05; C12M 47/04; C12N 2509/10; C12N 5/0653
See application file for complete search history.

(56) References Cited

U.S. PATENT DOCUMENTS

| | | | | |
|---|---|---|---|---|
| 5,372,945 A | * | 12/1994 | Alchas | C12M 45/09 435/308.1 |
| 5,409,833 A | * | 4/1995 | Hu | C12M 45/05 435/308.1 |
| 7,708,152 B2 | * | 5/2010 | Dorian | B01F 33/251 210/512.3 |

(Continued)

FOREIGN PATENT DOCUMENTS

| | | |
|---|---|---|
| GB | 2587257 B | 9/2021 |
| WO | WO 2003/053346 A2 | 7/2003 |

(Continued)

OTHER PUBLICATIONS

Combined Search and Examination Report for British Application No. GB 2008023.0 dated Sep. 30, 2020; 5 pages.

(Continued)

*Primary Examiner* — Kai H Weng
(74) *Attorney, Agent, or Firm* — Endurance Law Group PLC

(57) ABSTRACT

Disclosed are methods and devices for processing lipoaspirate that include mechanically-processing harvested lipoaspirate in a liposuction filter canister. In some embodiments, the devices are liposuction devices that include a lipoaspirate processing unit for mechanically-processing lipoaspirate. The mechanical processing reduces the average size of adipose tissue pieces in the lipoaspirate without substantially rupturing lipocytes therein.

19 Claims, 9 Drawing Sheets

(56) References Cited

U.S. PATENT DOCUMENTS

| | | | |
|---|---|---|---|
| 8,100,874 B1* | 1/2012 | Jordan | A61M 1/0001 604/319 |
| 2006/0051865 A1 | 3/2006 | Higgins et al. | |
| 2012/0003733 A1* | 1/2012 | Gueneron | C12M 29/06 366/331 |
| 2012/0214659 A1* | 8/2012 | Do | C12M 47/04 494/60 |
| 2013/0164731 A1* | 6/2013 | Cimino | A61M 1/0001 435/284.1 |
| 2015/0231244 A1 | 8/2015 | Chi et al. | |
| 2016/0304828 A1* | 10/2016 | Stanton | C12M 47/06 |
| 2019/0376882 A1* | 12/2019 | O'Neil | C12N 1/06 |
| 2020/0061259 A1 | 2/2020 | Taizou | |

FOREIGN PATENT DOCUMENTS

| | | |
|---|---|---|
| WO | WO 2011146924 A2 | 11/2011 |
| WO | WO 2014033209 A1 | 3/2014 |
| WO | WO 2015131087 A1 | 9/2015 |
| WO | WO 2018235102 A1 | 12/2018 |

OTHER PUBLICATIONS

International Search Report and Written Opinion for International Patent Application No. PCT/IB2021/051910 dated Jun. 1, 2021; 10 pages.

* cited by examiner

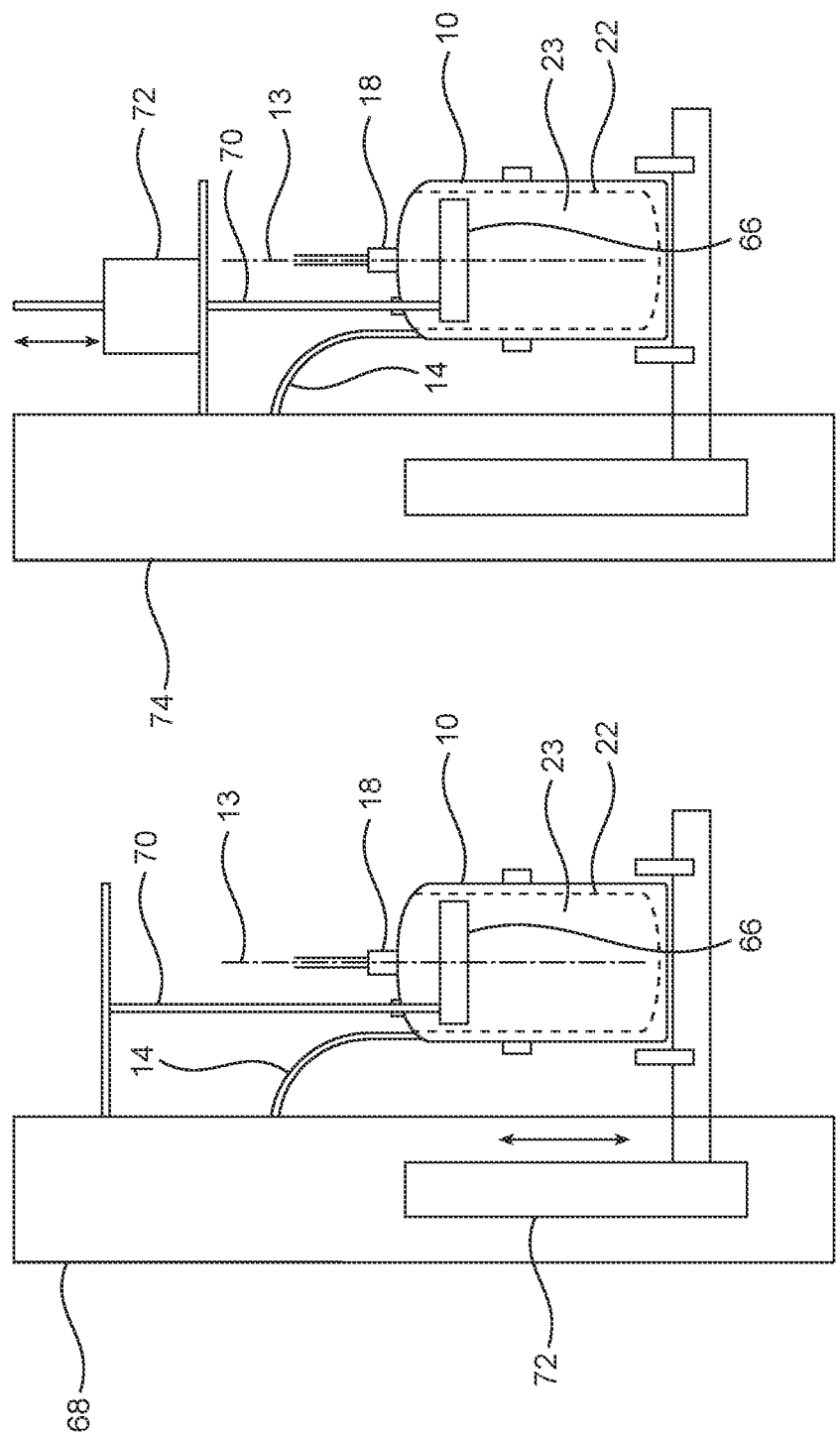

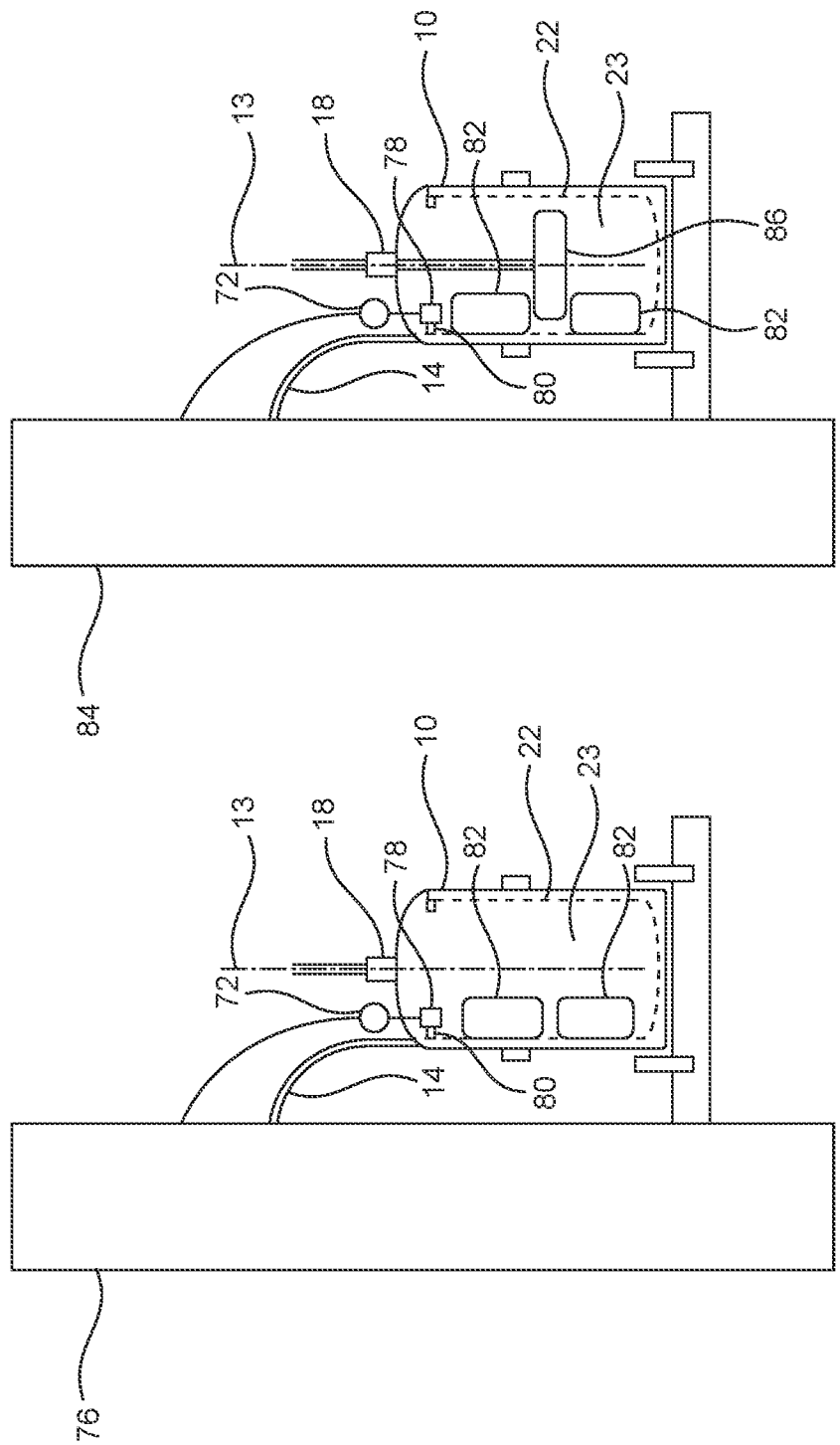

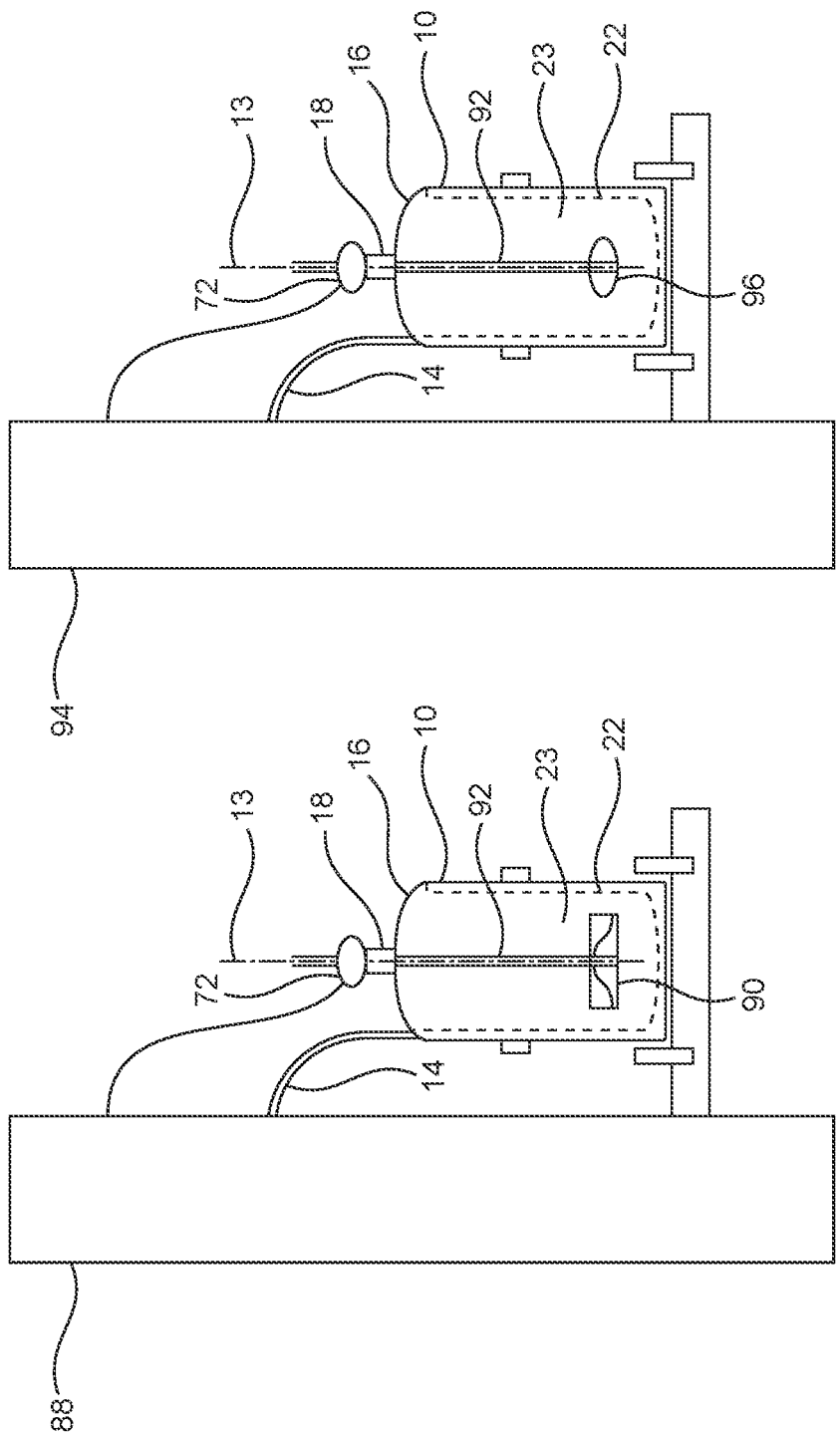

LIPOASPIRATE PROCESSING

RELATED APPLICATIONS

The subject application is a U.S. Continuation Patent Application of International Patent Application No. PCT/IB2021/051910, filed on Mar. 8, 2021, which claims priority to and the benefit of British Patent Application No. GB 2008023.0, filed May 28, 2020, and U.S. Provisional Application No. 62/986,806, filed on Mar. 9, 2020, the entire contents of which are hereby incorporated by reference.

TECHNICAL FIELD

The invention, in some embodiments, relates to the fields of aesthetics and/or medicine and, more particularly but not exclusively, to methods and devices for processing lipoaspirate.

BACKGROUND

Liposuction is a well-known method for aesthetic body-shaping where portions of subcutaneous adipose tissue are harvested from a part of the body of a subject as a lipoaspirate by suction through a cannula. Typically, suction is accompanied by simultaneous irrigation with an aqueous tumescent solution.

The harvested lipoaspirate comprises adipose tissue together with fluid waste including blood and tumescent solution.

Autologous Fat Transfer (AFT)

Often, harvested lipoaspirate is used for autologous fat transfer (AFT). For AFT, the fluid waste is removed from the harvested lipoaspirate and the remaining lipoaspirate washed one or more times with an aqueous washing solution, leaving a clean lipoaspirate consisting essentially of pieces of adipose tissue. The clean lipoaspirate is injected into a portion of the body, in some instances as-is and, in other instances, subsequent to a homogenization step performed by transferring the clean lipoaspirate back-and-forth between two coupled syringes to reduce the size of the adipose tissue pieces.

Stromal Vascular Fraction (SVF)

It has become accepted to process at least some harvested lipoaspirate to produce a stromal vascular fraction (SVF), which includes adipose-derived stromal cells (ASCs) useful for various purposes including: regenerative medicine, wound healing (e.g., post-radiotherapy wound-healing), treating osteoarthritis and treating autoimmune disease (e.g., scleroderma, lichen sclerosis). To this end, an amount of lipoaspirate (usually clean lipoaspirate) is processed (enzymatically and/or mechanically) to disintegrate the adipose tissue and release ASCs and the like that are in the tissue. The disintegrated adipose tissue is centrifuged to separate the lighter fatty remnants from the intact ASCs which settle at the bottom of the centrifuge vessel as an SVF pellet. The SVF pellet is suspended in an aqueous solution to separate ASCs from contaminants and again centrifuged, thereby providing a purified SVF pellet. The purified SVF pellet can be suspended in an aqueous solution and used therapeutically as-is. Preferably, the purified SVF pellet is cultured in a medium that keeps the ASCs viable while eliminating non-ASCs. After a sufficient culturing time (typically a few days), the thus-purified ASCs can be used therapeutically.

Enriched Lipoaspirate for Improved AFT

One of the challenges of AFT as described above is resorption of a substantial portion of the transplanted adipose tissue. Such resorption can lead to poor aesthetic results and often requires that an AFT procedure be repeated multiple times to achieve a desired aesthetic effect.

It has been found that it possible to perform improved AFT by using a lipoaspirate that is enriched by the addition of an SVF or ASCs prior to injection into the body. When the enriched lipoaspirate is transferred to the body in the usual way, there is reduced resorption and increased transplanted fat retention.

In a typical improved AFT procedure, a relatively large quantity of lipoaspirate is harvested by liposuction for body-shaping (~1000 ml). A small amount (typically ~100 ml) of the harvested lipoaspirate is processed to yield an SVF pellet, typically ~1% w/w of the processed lipoaspirate. The SVF, or ASCs isolated therefrom, is added to an amount of unprocessed clean lipoaspirate (typically 100 ml, optionally homogenized as described above) to provide enriched lipoaspirate which is then used for improved AFT. As a result of the enrichment, improved AFT is more successful and provides better results than AFT using non-enriched lipoaspirate.

It would be useful to find a simple manner to process a lipoaspirate that can be used for AFT which has one or more advantages over known methods of lipoaspirate processing.

SUMMARY OF THE INVENTION

Some embodiments of the invention herein relate to methods and devices for processing lipoaspirates, in some embodiments to be suitable for AFT and in some embodiments to make an SVF.

According to an aspect of some embodiments of the invention, there is provided a method of processing lipoaspirate, comprising:
   a. receiving a lipoaspirate harvested from a subject in a liposuction filter canister;
   b. subsequent to 'a', mechanically processing (in some embodiments, vortex-mixing) the lipoaspirate inside the liposuction filter canister to mix the lipoaspirate, the mechanical processing reducing the average size of adipose tissue pieces in the lipoaspirate without substantially rupturing lipocytes therein; and
   c. subsequent to 'b', draining fluid released from the lipoaspirate by the mechanical processing from the liposuction filter canister fluid,
thereby providing processed lipoaspirate contained in the liposuction filter canister.

As used herein, "mechanically processing" means that the lipoaspirate is caused to move relative to the filter liner of the liposuction filter canister, the motion sufficient to break-up the pieces of adipose tissue in the lipoaspirate so that the average size of the pieces of adipose tissue in the lipoaspirate is reduced. In some embodiments, the average size of the adipose tissue pieces is reduced to 50% of the original, to 25% of the original and even to 10% of the original.

As used herein, "without substantially rupturing lipocytes therein" means that at least 90%, at least 95% and even at least 98% of the lipocytes in the lipoaspirate are not ruptured as a result of the mechanical processing.

In some embodiments, 'b' starts only when 'a' is complete, that is to say, all the desired harvested lipoaspirate is received ('a') prior to starting the mechanical processing ('b'). Alternately, in some embodiments, mechanical processing ('b') is started when at least some harvested lipoaspirate is received ('a'). As a result, in such alternate embodiments mechanical processing is performed concurrently with receipt of some harvested lipoaspirate.

Any suitable manner of mechanical processing that reduces the average size of the pieces of adipose tissue but is gentle enough to avoid substantial rupturing of lipocytes may be used in implementing the teachings herein. In some embodiments, the mechanical processing is selected from the group consisting of: vortex mixing the lipoaspirate in the canister; vibrating the lipoaspirate in the canister; and mechanically-mixing the lipoaspirate in the canister. Especially preferred is vortex-mixing that has been experimentally shown to provide high-quality processed lipoaspirate, is currently believed to more easily be kept aseptic and is easy to implement.

Thus, according to an aspect of some embodiments of the invention, there is also provided a method of processing lipoaspirate, comprising:
 a. receiving a lipoaspirate harvested from a subject in a liposuction filter canister;
 b. subsequent to 'a', vortex-mixing the lipoaspirate inside the liposuction filter canister to mix the lipoaspirate; and
 c. subsequent to 'b', draining fluid released from the lipoaspirate by the vortex-mixing from the liposuction filter canister,
thereby providing processed lipoaspirate contained in the liposuction filter canister.

Thus, according to an aspect of some embodiments of the invention, there is also provided a method of processing lipoaspirate, comprising:
 a. receiving a lipoaspirate harvested from a subject in a liposuction filter canister;
 b. subsequent to 'a', mechanically-mixing the lipoaspirate inside the liposuction filter canister to mix the lipoaspirate; and
 c. subsequent to 'b', draining fluid released from the lipoaspirate by the mechanical mixing from the liposuction filter canister,
thereby providing processed lipoaspirate contained in the liposuction filter canister.

In some embodiments, the mechanical processing, such as vortex mixing, is applied within 60 minutes of harvesting of the lipoaspirate.

In some embodiments, prior to and/or during the mechanical processing, e.g. vortex mixing, a volume of aqueous solution is added to the liposuction filter canister.

In some embodiments, the mechanical processing is vortex mixing that is performed at not more than 3000 rpm and even not more than 1000 rpm.

In some embodiments, the mechanical processing is vortex mixing that is performed for not more than 30 minutes.

In some embodiments, the mechanical processing is vortex mixing that is performed for not less than 60 seconds.

In some embodiments, the liposuction filter canister is in a state of being functionally-associated with a fluid drainage module during the mechanical processing, that is to say, that to perform mechanical processing there is no need to disconnect an already-connected fluid drainage module.

In some embodiments, the fluid drainage module is a component of a liposuction vacuum module.

In some embodiments, the method of processing lipoaspirate further comprises: subsequent to the draining 'c', transferring the lipoaspirate to an autologous fat transfer (AFT) device. In some embodiments, the method of processing lipoaspirate further comprises transplanting the transferred lipoaspirate to a subject using the AFT device. Alternatively, in some embodiments, a step of transplanting the transferred lipoaspirate is a method of surgical treatment and is outside the scope of the claims.

In some embodiments, the lipoaspirate in the liposuction filter canister is not washed subsequent to the mechanical processing, such as vortex mixing, 'b' and prior to the transferring of the lipoaspirate to an AFT device.

In some embodiments, the lipoaspirate in the liposuction filter canister is not centrifuged subsequent to the mechanical processing, such as vortex mixing, 'b' and prior to the transferring of the lipoaspirate to an AFT device.

In some embodiments, the liposuction canister filter has a volume of not less than 50 ml and not more than 10,000 ml.

In some embodiments, an amount of the harvested lipoaspirate received in the liposuction filter canister is not less than 50 ml and not more than 10,000 ml.

In some embodiments, the lipoaspirate was harvested from a subject using a method selected from the group consisting of laser-assisted liposuction, ultrasound-assisted liposuction and RF-assisted liposuction.

In some embodiments, the laser-assisted liposuction was performed using a laser wavelength within the range 800-1600 nm, and in some embodiments with the range 1400-1500 nm.

In some embodiments, the laser-assisted liposuction was performed using a radially-irradiating optical fiber.

Any suitable cannula having any suitable size may be used in implementing the teachings herein, in some embodiments, the lipoaspirate was harvested using a cannula with an internal diameter of at least 2 mm and not more than 5 mm.

Any suitable suction pressure may be used for harvesting the lipoaspirate. In some embodiments, the lipoaspirate was harvested using a suction pressure of at least 20 kP and not more than 98 kP.

In some embodiments, the method further comprises: d. subsequent to 'c', applying additional mechanical processing (such as vortex mixing or any other option listed above) to the lipoaspirate contained in the liposuction filter canister to mix the lipoaspirate, the additional mechanical processing reducing the average size of adipose tissue pieces in the lipoaspirate without substantially rupturing lipocytes therein.

In some embodiments, the method further comprises: subsequent to the additional mechanical processing 'd', transferring the lipoaspirate to an autologous fat transfer (AFT) device. In some embodiments, the method further comprises transplanting the transferred lipoaspirate to a subject using the AFT device. Alternatively, in some embodiments, a step of transplanting the transferred lipoaspirate is a method of surgical treatment and is outside the scope of the claims. In some embodiments, the method further comprises: e. subsequent to 'd', isolating fluid released from the lipoaspirate consequent to the additional mechanical processing as an SVF fluid.

Embodiments of the method may be implemented using any suitable device or combination of devices. In some preferred embodiments, the method is implemented using a liposuction device according to the teachings herein.

According to an aspect of some embodiments of the invention, there is also provided a liposuction device that, in some embodiments, is exceptionally suitable for implementing embodiments of the method according to the teachings herein.

Thus, according to an aspect of some embodiments of the invention, there is also provided a liposuction device configured for performing liposuction by drawing adipose tissue from a body as a lipoaspirate through a cannula and transferring (also termed "transporting" in the priority document) at least some the harvested adipose tissue into a liposuction filter canister functionally associated with the liposuction device, the device comprising: a lipoaspirate processing unit, the lipoaspirate processing unit configured, when activated, to mechanically process lipoaspirate contained inside a liposuction filter canister functionally-associated with the liposuction device, the mechanically processing reducing the average size of adipose tissue pieces in the lipoaspirate without substantially rupturing lipocytes therein. Without wishing to be held to any one theory, it is currently believed that such gentle mechanical processing produces a relatively homogenous processed lipoaspirate that includes various non-factors (e.g., SVF) in a form that is accessible for use when transplanted.

In some embodiments, the liposuction device further comprises: a liposuction vacuum module attachable to a liposuction filter canister which is functionally-associated with the liposuction device through a vacuum port thereof, the liposuction vacuum module configured, when attached to a liposuction filter canister and activated, to effect liposuction through the liposuction filter canister and through a liposuction probe functionally associated therewith, thereby allowing trapping of harvested adipose tissue (i.e., adipose tissue that is harvested as a consequence of the liposuction) in a filter liner of the attached filter canister. In some embodiments, the liposuction device is configured to allow activation of the lipoaspirate processing unit to mechanically process the contents of a liposuction filter canister functionally associated with the liposuction device while the liposuction filter canister is attached to the liposuction vacuum module.

In some embodiments, the liposuction device comprises a fluid drainage module different from the liposuction vacuum module, the fluid drainage module attachable to a liposuction filter canister that is functionally-associated with the liposuction device through a drainage port thereof, the fluid drainage module configured, when attached to such a liposuction filter canister and activated, to remove liquids from a container of the attached liposuction filter canister. In some embodiments, the liposuction device is configured to allow activation of the lipoaspirate processing unit to mechanically process the contents of a liposuction filter canister functionally associated with the liposuction device while the liposuction filter canister is attached to said fluid drainage module.

In some embodiments, the liposuction device further comprises a liposuction probe having a distal end attachable to a liposuction cannula and a proximal end attachable to a liposuction filter canister that is functionally-associated with the liposuction device through an aspirate inlet thereof, the liposuction probe configured to direct liposuction aspirate harvested via an attached liposuction cannula from the distal end of the probe through the proximal end of the probe into a container of an attached liposuction filter canister. In some embodiments, the liposuction device is configured to allow activation of the lipoaspirate processing unit to mechanically process the contents of a liposuction filter canister that is functionally associated with the liposuction device while the liposuction filter canister is attached to the liposuction probe.

In some embodiments, the liposuction device further comprises a washing module attachable to a liposuction filter canister functionally-associated with the liposuction device through an access port thereof, the washing module configured to add an amount of liquid (e.g., washing solution) into a container of an attached liposuction filter canister, preferably a metered amount of liquid. In some embodiments, the liposuction device is configured to allow activation of the lipoaspirate processing unit to mechanically process the contents of a liposuction filter canister functionally-associated with the liposuction device while the liposuction filter canister is attached to the washing module.

In some embodiments, the liposuction device further comprises a controller configured to automatically process lipoaspirate contained in a liposuction filter canister that is functionally associated with the liposuction device, the automatic processing comprising activation of the lipoaspirate processing unit, the fluid drainage module and/or the washing module in a desired order for a desired duration. In some embodiments, the controller is configured to activate only one of the three units/modules. In some embodiments, the controller is configured to activate only two of the three units/modules. In some embodiments, the controller is configured to activate all three units/modules.

In some embodiments, the liposuction device further comprises a liposuction filter canister functionally-associated with the liposuction device, the liposuction filter canister including: a container; a longitudinal axis, a canister vacuum port (preferably attached to the liposuction vacuum module); a cap for sealingly closing the container; a canister aspirate inlet (preferably attached to a proximal end of the liposuction probe; an access port (preferably attached to the washing module); and a filter liner that defines an inner volume inside the container, the filter canister configured so that when attached to the liposuction probe through the canister aspirate inlet and attached to the liposuction vacuum module through the vacuum port, activation of the liposuction vacuum module allows effecting liposuction through the liposuction probe and trapping of harvested adipose tissue in the filter liner (i.e., in the inner volume defined by the filter liner). In some embodiments, the liposuction filter canister further comprises a drainage port attachable to (and preferably attached to) the liquid drainage module, the drainage port allowing the removal of liquid held in the container outside of the filter liner. In some embodiments, the drainage port is the canister vacuum port. Alternately, in some embodiments, the drainage port is a component different from the canister vacuum port. The filter canister is any suitable size, e.g., as recited below.

Vortex Mixing Unit

In some preferred embodiments, the lipoaspirate processing unit comprises a vortex mixing unit, the vortex-mixing unit configured, when activated, to produce and apply vortex-inducing motion to a liposuction filter canister functionally-associated with the liposuction device, the vortex-inducing motion effective to mechanically process lipoaspirate contained in the inner volume of the filter canister.

In some embodiments, the vortex-mixing unit includes an engagement component that transfers at least some vortex-inducing motion produced by the vortex-mixing unit to a liposuction filter canister functionally-associated with the liposuction device when the vortex-mixing unit is activated.

In some embodiments, the vortex-mixing unit is configured so that a bottom of a filter canister functionally-associated with the liposuction device rests on the vortex-mixing unit. Such an embodiment is depicted in FIGS. 2A, 2B and 2C.

In some such embodiments, the vortex-mixing unit includes a flat upper surface on which a flat bottom of a filter canister functionally-associated with the liposuction device rests. Such an embodiments is depicted in FIGS. 2A and 2B. In some such embodiments, the flat upper surface is defined by an upper surface of an engagement component of the vortex-mixing unit. Such an embodiment is depicted in FIG. 2A.

In some such embodiments, the engagement component at least partially encircles a bottom of filter canister resting on the flat upper surface. Such an embodiment is depicted in FIG. 2B.

In some such embodiments, the vortex-mixing unit includes a non-flat upper surface on which the non-flat bottom of a liposuction filter canister functionally-associated with the liposuction device rests, the non-flat upper surface encircling at least part of a bottom portion of a filter canister. Such an embodiment is depicted in FIG. 2C.

In some embodiments, the vortex-mixing unit is configured, when activated, to vortex-mix the contents of a liposuction filter canister functionally-associated with the liposuction device at not more than 3000 rpm, not more than 2000 rpm, not more than 1000 rpm, and in some embodiments even not more than 700 rpm. In some embodiments, the vortex-mixing unit is configured, when activated, to vortex-mix the contents of a liposuction filter canister functionally-associated with the liposuction device at not less than 60 rpm, and in some embodiments even not less than 100 rpm.

In some embodiments, the vortex-mixing unit and/or a controller of the liposuction device are configured to allow vortex-mixing of the contents of a liposuction filter canister functionally-associated with the liposuction device for a period of not more than 30 minutes, not more than 20 minutes, not more than 10 minutes and even not more than 7 minutes.

In some embodiments, the vortex-mixing unit and/or the controller are configured to allow vortex-mixing of the contents of a liposuction filter canister functionally-associated with the liposuction device for a period of not less than 30 seconds and even not less than 60 seconds.

Vibration Unit

In some embodiments, the lipoaspirate processing unit comprises a vibration unit, the vibration unit configured, when activated, to produce and apply vibrations to lipoaspirate contained in the inner volume of a liposuction filter canister functionally-associated with the liposuction device, the vibrations effective to mechanically process the lipoaspirate.

In some embodiments, the vibration unit comprises at least one sonic transmitter probe configured to be positioned inside an inner volume defined by the filter liner of a liposuction filter canister functionally-associated with the liposuction device. In such embodiments, during use the probe is at least partially immersed in the lipoaspirate. Such an embodiment is depicted in FIGS. 3A and 3B.

In some embodiments, the vibration unit comprises a sonic transmitter configured to physically-associate with a filter liner of a liposuction filter canister functionally-associated with the liposuction device so that when activated, said sonic transmitter causes a physically-associated filter liner to vibrate. The vibrating filter liner transfers the vibrations from the sonic transmitter to the lipoaspirate held therein. Such an embodiment is depicted in FIG. 3C.

It is important to note that, in some such embodiments, the sonic transmitter is a component of a liposuction filter canister and the liposuction device is configured, for example includes electrical connectors, to allow operation of the sonic transmitter of the liposuction canister in accordance with the teachings herein.

Mechanical Mixing

In some embodiments, the lipoaspirate processing unit comprises:
a mechanical mixing component configured to be positioned inside an inner volume defined by a filter liner of a liposuction filter canister functionally-associated with the liposuction device; and
a mixing motor configured to move the mechanical mixing component relative to lipoaspirate contained in the volume to thereby mechanically-mix the lipoaspirate, the mechanical mixing effective to mechanically process the lipoaspirate.

In some embodiments, the mixing motor is configured so that the relative motion of the mechanical mixing component to the liposuction filter canister comprises, or is, translation in parallel to the longitudinal axis of the liposuction filter canister. Such an embodiment is depicted in FIGS. 4A, 4B and 4C. In some such embodiments, the filter canister is moved in parallel to the longitudinal axis (FIG. 4B). Additionally or alternatively, in some such embodiments, the mechanical mixing component is moved in parallel to the longitudinal axis (FIG. 4C). In some such embodiments, the mechanical mixing component comprises, or is, a flow-restricting barrier such as a pervious plunger (FIG. 4A). In some such embodiments, the mechanical mixing component, such as a flow-restricting barrier, is a component of the filter canister. In some such embodiments, the mechanical mixing component, such as a flow-restricting barrier, is not a component of the filter canister.

Alternately or additionally, in some embodiments, the mixing motor is configured to rotate the filter liner relative to a container of the liposuction filter canister around an axis parallel to the longitudinal axis of the liposuction canister. Such an embodiment is depicted in FIGS. 4D and 4E. In some such embodiments, the mechanical mixing component comprises mixing elements affixed to an inner surface of the filter liner and protruding into the inner volume that rotate together with the filter liner (FIGS. 4D and 4E). Additionally or alternatively, in some embodiments the mechanical mixing component comprises mixing elements that do not rotate together with the filter liner (FIG. 4E).

Alternately or additionally, in some embodiments the mixing motor is configured to rotate a mechanical mixing component that is separate from the filter liner located inside inner volume. Such an embodiment is depicted in FIGS. 4F, 4G and 4H. Any suitable type, or combination of types, of mechanical mixing component, e.g., one or more components selected from the group consisting of an impeller (FIG. 4F), a propellor (FIG. 4G) and a paddle (FIG. 4H). In some such embodiments, the mechanical mixing component is a component of the filter canister. In some such embodiments, the mechanical mixing component is not a component of the filter canister.

In some embodiments, the liposuction device is selected from the group consisting of: a laser-assisted liposuction device; an ultrasound-assisted liposuction device; and an RF-assisted liposuction device.

In some embodiments, the liposuction device is a laser-assisted liposuction device, configured to irradiate adipose tissue with laser light having a wavelength within the range 800 nm and 1600 nm during liposuction. In some embodiments, the laser wavelength is within the range of 1400 nm-1500 nm, 1450-1490 nm and even within the range of 1460-1480 nm, for example a laser wavelength of 1470 nm as is used in some commercially-available laser-assisted liposuction devices.

In some embodiments, the liposuction device is a laser-assisted liposuction device, configured to perform liposuction using a radially-irradiating optical fiber.

In some embodiments, the liposuction device is configured to harvest lipoaspirate through a cannula with an internal diameter of at least 2 mm and not more than 5 mm.

In some embodiments, the liposuction device is configured to apply a suction pressure of at least 20 kP and not more than 98 kP.

Liposuction Filter Canisters of the Teachings Herein

In some embodiments, the teachings herein are implemented using a liposuction filter canister according to the teachings herein.

According to an aspect of some embodiments of the teachings herein, there is provided a liposuction filter canister functionally-associatable with a liposuction device, comprising: a container having a longitudinal axis; a canister vacuum port functionally-associatable with a liposuction vacuum module of a liposuction device; a cap for sealingly closing the container; a canister aspirate inlet attachable to a proximal end of a liposuction probe; and a filter liner that defines an inner volume inside the container, the filter canister configured so that when attached to a liposuction probe through the canister aspirate inlet and attached to a liposuction vacuum module through the vacuum port, activation of the attached liposuction vacuum module allows effecting liposuction through the liposuction probe and trapping of harvested adipose tissue in the inner volume defined by the filter liner, the liposuction filter canister further comprising at least one of:

i. a sonic transmitter probe located inside the inner volume, the probe configured to vibrate at an acoustic frequency of not more than 10 kHz when activated (so that such activation leads to mechanical processing of lipoaspirate held in the inner volume);
  ii. a sheath protruding into the inner volume, the sheath configured for accepting a sonic transmitter probe (so that when the probe is activated to vibrate, the vibrations pass through the sheath, leading to mechanical processing of lipoaspirate held in the inner volume);
  iii. a sonic transmitter physically-associated with the filter liner, the sonic transmitter configured to cause the filter liner to vibrate at an acoustic frequency of not more than 10 kHz when activated (so that such activation leads to mechanical processing of lipoaspirate held in the inner volume); and
  iv. a mechanical mixing component located inside the inner volume, the mechanical mixing component configured to be functionally associated with a mixing motor and, when the mixing motor is activated, to move relative to lipoaspirate contained in the inner volume (so that such relative motion leads to mechanical processing of lipoaspirate held in the volume).

In some embodiments, the mechanical mixing component is configured to move with a motion vector that is, or includes, a component parallel to the longitudinal axis. (e.g., the mechanical mixing component is, or comprises, a flow-restricting barrier such as a partially-pervious plunger).

In some embodiments, the mechanical mixing component is configured to rotate relative to the container (e.g., the mechanical mixing component comprises or is a propellor, an impeller or a paddle; or the filter liner is configured to rotate).

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale. In the Figures:

FIGS. 4A-4H are schematic depictions of components of embodiments of devices useful for implementing embodiments of the methods according to the teachings herein, the devices configured for mechanical mixing.

DETAILED DESCRIPTION

Figure 1:
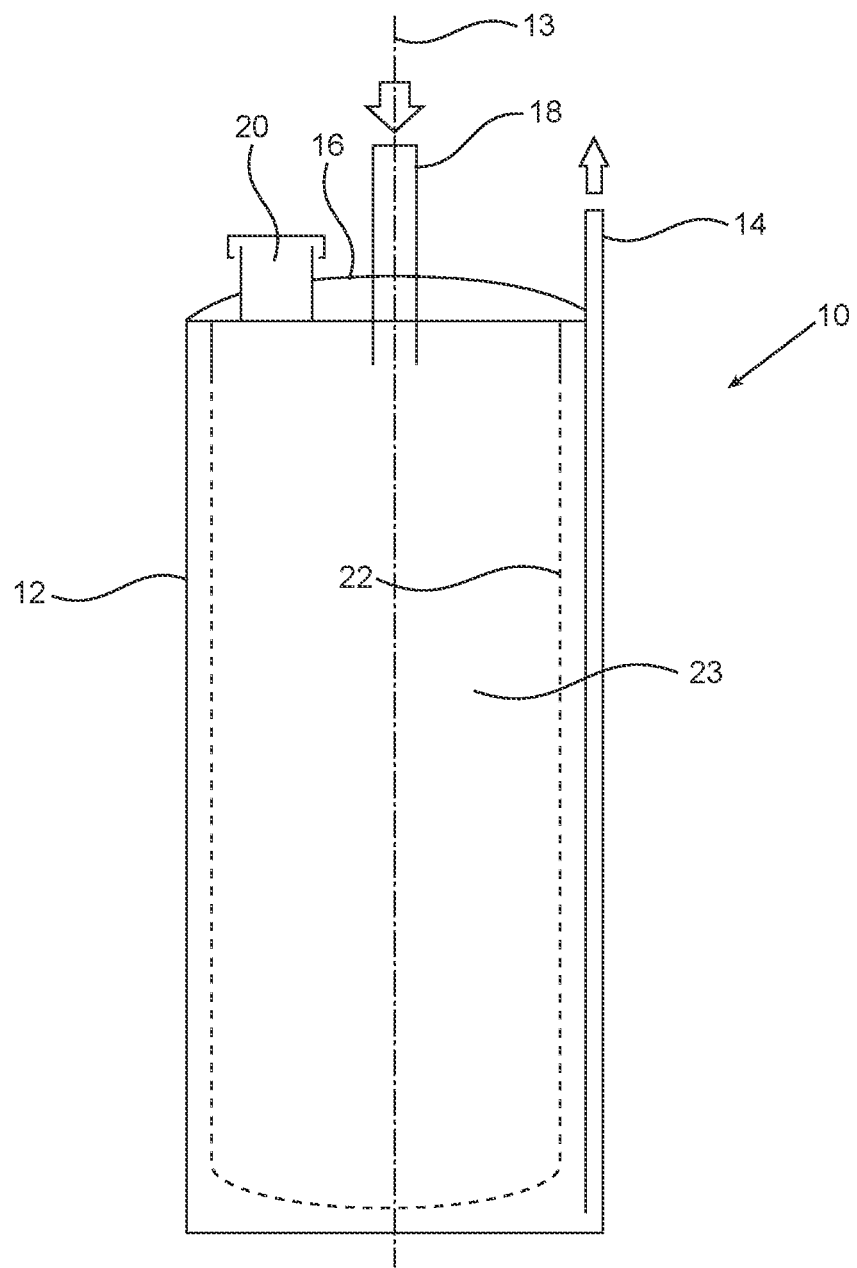
FIG. 1 is a schematic depiction of an embodiment of a liposuction filter canister useful for implementing the teachings herein.

Some embodiments of the invention herein relate to methods and devices for processing lipoaspirate, in some embodiments to be suitable for AFT (autologous fat transfer) and in some embodiments to make an SVF (stromal vascular factor).

The principles, uses and implementations of the teachings of the invention may be better understood with reference to the accompanying description and figures. Upon perusal of the description and figures present herein, one skilled in the art is able to implement the teachings of the invention without undue effort or experimentation. In the figures, like reference numerals refer to like parts throughout.

Before explaining at least one embodiment of the invention in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

As is known in the art, tissue, including the adipose tissue that makes up lipoaspirate, can be mechanically processed in many ways for example, using a meat grinder (U.S. Pat. No. 5,731,199), a perforated rasp (WO 2016/097960), forcing the fat through perforations (WO 2017/180076, WO 2019/125324) and using a high speed rotating blade as a "food processor" (WO 2016/199149).

The Inventors, after studying the art and performing experiments, conclude that mechanical processing of lipoaspirate can be considered as having a combination of three separate effects.

The first of the three effects is homogenization of the lipoaspirate, reducing the size of the adipose tissue pieces to produce a more fluid lipoaspirate including viable lipocytes that can more easily and more accurately be injected during an AFT procedure, providing improved aesthetic results.

The second of the three effects is damaging the adipose tissue and rupturing lipocytes in the lipoaspirate, leading to the production and/or release of harmful factors such as pro-inflammatory and toxic materials including cell/tissue fragments as well as hormones and other factors. The Inventors believe that such harmful factors contribute in a large part to the challenges and complications of known AFT procedures including inflammation and post-transplantation resorption of transplanted fat.

The third of the three effects is the release of beneficial factors from the adipose tissue. Beneficial factors include stem cells and the like that make up the SVF, well known for having therapeutic properties. As discussed in the introduction, subsequent to mechanical or enzymatic processing, the beneficial factors can be isolated for therapeutic use as-is or for implementing improved AFT.

In the art, the three effects are considered in isolation, each for a specific use:

For AFT, modest homogenization of lipoaspirate is performed to produce a more fluid lipoaspirate that can be more accurately transferred to a subject using a smaller needle during AFT. Additionally, whether or not homogenized, lipoaspirates that are used for AFT are rigorously and repeatedly washed with a washing solution to remove harmful factors.

When it desired to provide SVF or isolated ASCs from a harvested lipoaspirate, the lipoaspirate is vigorously processed to completely destroy the adipose tissue and lipocytes to ensure that the maximal amount of ASCs are released from the tissue, followed by extensive purification (including centrifugation, washing with a washing solution and culturing) to remove harmful factors and produce therapeutically-useful SVF or ASCs. As discussed above, one use of such purified SVF/ASCs is to enrich lipoaspirate for improved AFT.

The Inventors have discovered and now disclose a method for processing lipoaspirate which balances these three effects, yielding a lipoaspirate that is apparently enriched. Specifically, the Inventors have discovered that it is possible to gently mechanically process a harvested lipoaspirate to produce a lipoaspirate that is apparently enriched with beneficial factors yet has few, if any, harmful factors. In some embodiments, the methods yields a processed lipoaspirate that increases the success of AFT performed using the processed lipoaspirate, for example by one or both of reducing the amount of post-AFT inflammation and reducing resorption of transplanted fat. The method is exceptionally suitable for use with lipoaspirate harvested using gentle liposuction methods such as laser-assisted liposuction. Further, the Inventors have found that some embodiments of the method allow for aseptic preparation of AFT in a clinical setting with little human intervention.

In some embodiments, the method is quicker than some known methods, allowing for lipoaspirate harvesting, processing and subsequent improved AFT in a relatively short time that is suitable for a single-session at an aesthetic or therapeutic clinic. It is believed that in some embodiments a shorter harvest-to-AFT time reduces stress on transferred tissue which can further increase the success of the AFT.

In some embodiments, the method is performed in a way that more easily prevents contamination, allowing for safer AFT with a reduced chance of inflammation and even sepsis, increasing customer satisfaction and reducing liability for a clinic that practices the method.

In some embodiments, the method is easy to perform, even for a person who is pressed for time or not an expert laboratory technician, for example a nurse or an assistant in a clinic that practices the method.

In some embodiments, the method is easy to at least partially automate, reducing the workload required from personnel and in some embodiments improving repeatability and consistency of the results, even when performed by a person who is not an expert laboratory technician.

Method for Processing Lipoaspirate

According to an aspect of some embodiments of the teachings herein, there is provided a method of processing lipoaspirate, comprising:
 a. receiving a lipoaspirate harvested from a subject contained in a liposuction filter canister;
 b. subsequent to 'a', mechanically processing (in some embodiments, vortex-mixing) the lipoaspirate inside the liposuction filter canister to mix the lipoaspirate, the mechanical processing reducing the average size of adipose tissue pieces in the lipoaspirate without substantially rupturing lipocytes therein; and
 c. subsequent to 'b', draining fluid released from the lipoaspirate by the mechanical processing from the liposuction filter canister fluid, thereby providing processed lipoaspirate contained in the liposuction filter canister.

Receiving Lipoaspirate in a Liposuction Filter Canister

In 'a', lipoaspirate harvested from a subject is received in a liposuction filter canister. Preferably, the liposuction filter canister is a single-use sterile liposuction filter canister. Any suitable liposuction filter canister can be used, including commercially-available liposuction filter canisters such as the Contour™ canisters from Bemis® Health Care™, Sheboygan Falls, Wis., USA or Tissue-Trans® Filtron Units from Tulip® Medical Instruments, San Diego, Calif., USA. In some embodiments, the liposuction filter canister is a liposuction filter canister according to the teachings herein.

An exemplary liposuction filter canister 10 is schematically depicted in cross section in FIG. 1. Liposuction filter canister 10 includes a container 12, a longitudinal axis 13, a canister vacuum port 14, and a cap 16 that sealingly-closes container 12. Through cap 16 is a canister aspirate inlet 18 and a sealable access port 20. Held inside container 12 is a filter liner 22 (having filter holes, typically between 100 micrometers and 1000 micrometers) that defines an inner volume 23. Sealable access port 20 is an opening that can be optionally closed, preventing entry of contamination and air into container 12, but can be reversibly opened, allowing addition of materials (e.g., washing solution) or removal of materials (e.g., a sample of lipoaspirate held in filter liner 22).

For use (see FIGS. 2A-2D), canister 10 is functionally-associated with a liposuction device 24 by holding canister 10 in a filter canister holder 25, connecting canister vacuum port 14 to a liposuction vacuum module 26 of liposuction device 24 and connecting canister aspirate inlet 18 to a liposuction probe 28 at which distal end is found a liposuction cannula 30.

Vacuum module 26 is activated, producing suction at the liposuction inlets of cannula 30. When cannula 30 is contacted with in vivo adipose tissue, adipose tissue in drawn from the body into cannula 30 and transferred into canister 10 as lipoaspirate. Adipose tissue is trapped in inner volume 23 of filter liner 22 while liquid waste such as blood and tumescent solution pass through the filter holes of filter liner 22 and are removed into vacuum module 26, typically to be discarded. As a result, the lipoaspirate received in a liposuction filter canister such as 10 consists essentially of adipose tissue and is relatively free of liquid waste such as blood and/or tumescent solution.

Mechanical Processing of the Lipoaspirate

As discussed above, in 'b', lipoaspirate inside the liposuction filter canister is mechanically-processed (in some embodiments, vortex-mixed) to mix the lipoaspirate. The mechanical processing reduces the average size of adipose tissue pieces in the lipoaspirate without substantially rupturing lipocytes therein. As noted above, any suitable method of mechanical processing that is sufficient to break-up the pieces of adipose tissue but is gentle enough to avoid substantial rupturing of lipocytes may be used in implementing the teachings herein. In some embodiments, the mechanical mixing is selected from the group consisting of: vortex mixing the lipoaspirate in the canister; vibrating the lipoaspirate in the canister; and mechanically-mixing the lipoaspirate in the canister.

For brevity and clarity, the description that follows will discuss an embodiment where the mechanical processing is vortex-mixing. The description is applicable, mutatis mutandis, for other methods of mechanical processing.

In 'b', vortex-mixing is applied to the lipoaspirate that is held inside the liposuction filter canister, thereby vortex-mixing the lipoaspirate. Any suitable method and/or device may be used for vortex-mixing of the lipoaspirate.

Figure 2A:
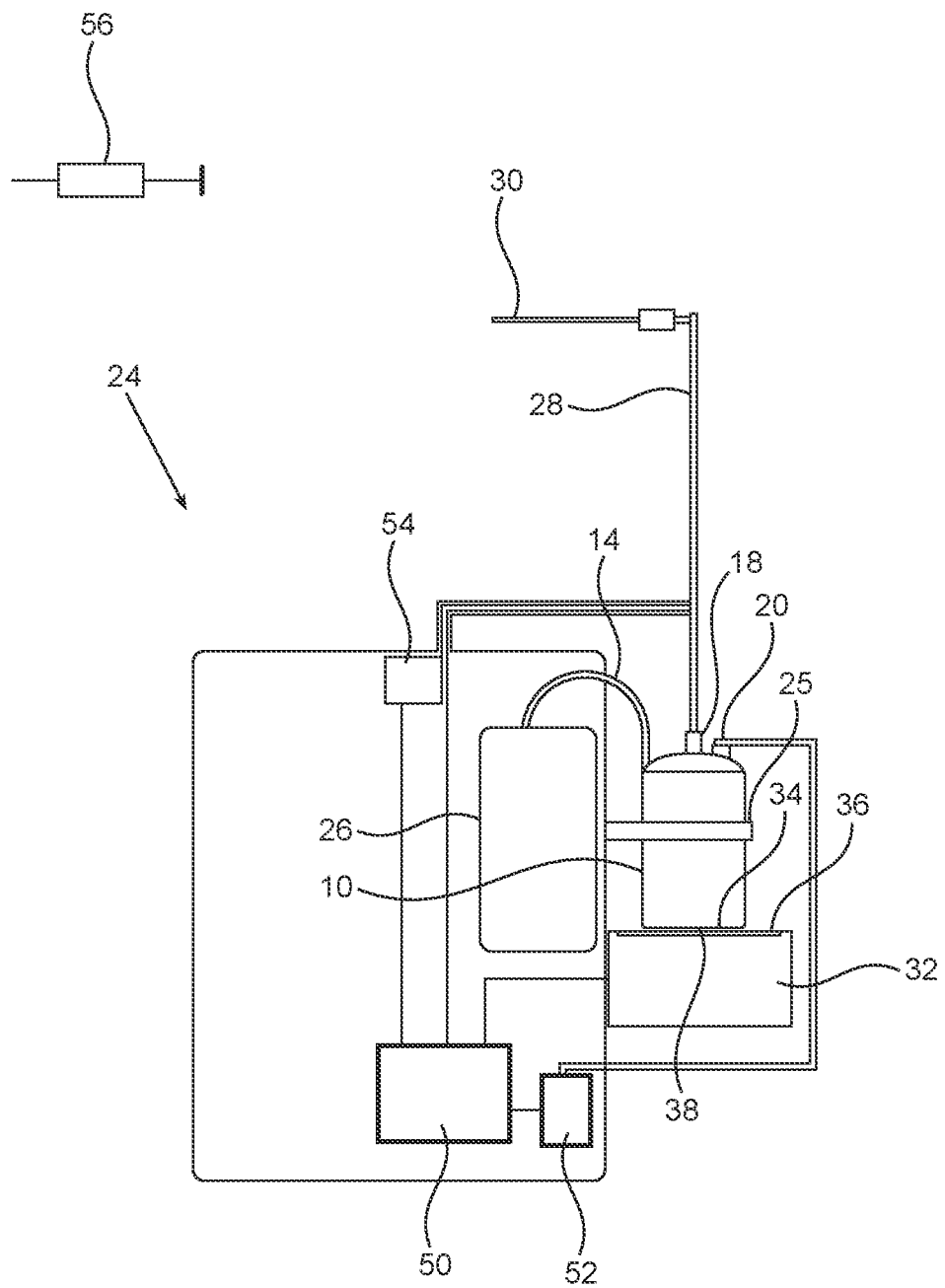
FIGS. 2A-2D are schematic depictions of embodiments of devices useful for implementing embodiments of the methods according to the teachings herein, the devices including a laser-assisted liposuction unit and a vortex-mixing unit.
Figure 2B:
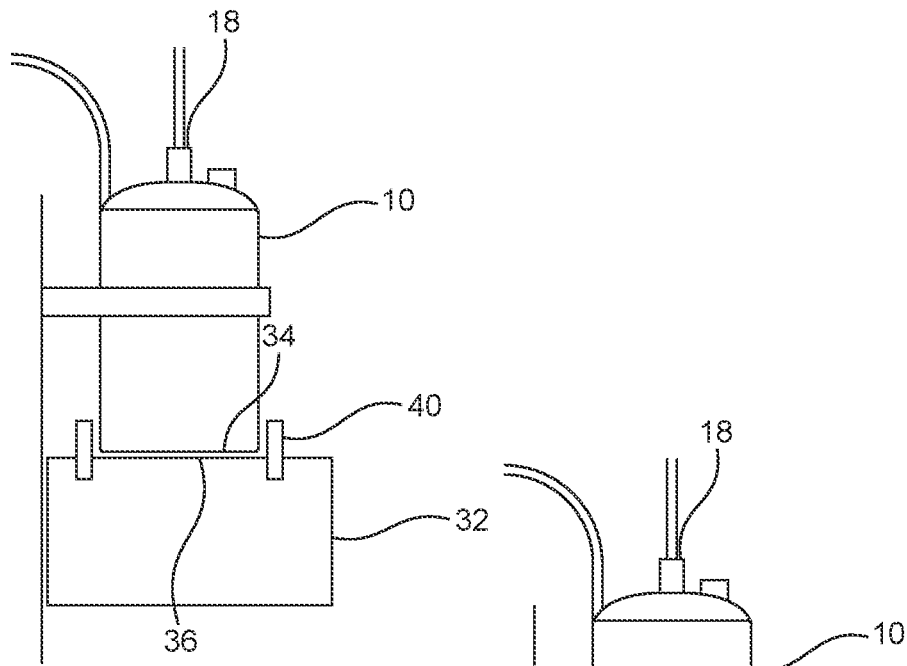
Figure 2C:
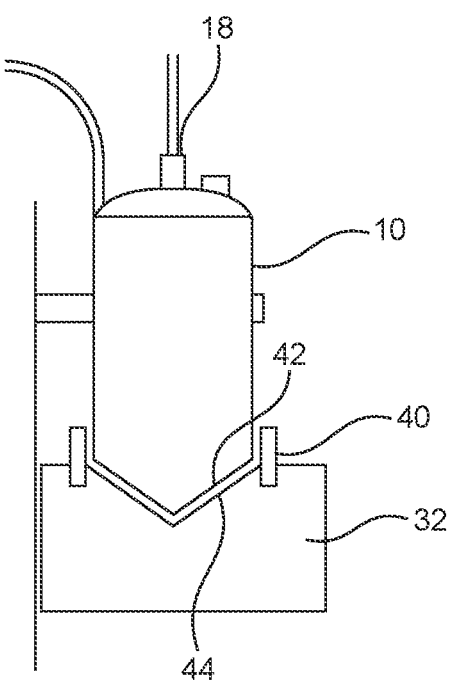

In some embodiments, the vortex-mixing is by a vortex-mixing unit on which the bottom of the filter canister container rests. FIGS. 2A, 2B and 2C depict embodiments having a vortex-mixing unit 32 on which the bottom of the container of filter canister 10 rests.

Figure 2D:
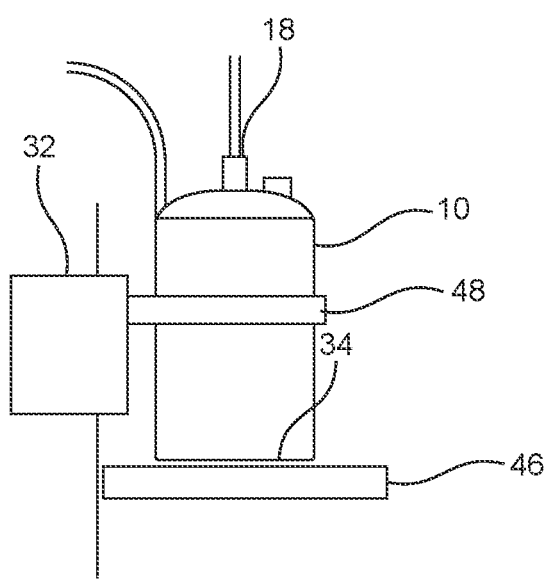

Alternatively or additionally, in some embodiments, the vortex-mixing is by a vortex-mixing unit which at least partially encircles at least a portion of the filter canister container. FIGS. 2B, 2C and 2D depict embodiments having a vortex-mixing unit 32 which at least partially encircles at least a portion of a filter canister 10. It is important to note that FIGS. 2, 3 and 4B-4H are drawn so that there is a gap between the bottom of a canister 10 and components of the depicted device, e.g., mixing unit 32. The gap is drawn for clarity and, in practice, the canister physically contacts the component.

As known to a person having ordinary skill in the art, a vortex-mixing unit is a unit that produces and applies motion to a vessel in which a fluid is held (e.g., a filter canister in which lipoaspirate is held), the applied motion inducing the formation of a vortex in the fluid, the vortex effective for mixing the fluid. In some embodiments, a vortex-mixing unit used for implementing the teachings herein includes an engagement component that transfers at least some of the vortex-inducing motion produced by the vortex-mixing unit to a filter canister held by the filter canister holder when the vortex-mixing unit is activated.

In FIG. 2A, a flat bottom 34 of filter canister 10 is depicted resting on a flat upper surface 36 of vortex-mixing unit 32. In FIG. 2A, flat upper surface 36 of vortex-mixing unit 32 is defined by the upper surface of the engagement component thereof, a rubber mat 38. When vortex-mixing unit 32 is activated, vortex-stirring inducing motion is transferred to filter canister 10 through the engagement component, rubber mat 38. In some similar embodiments, the engagement component is made of a material different from rubber, e.g., plastic or silicone.

In FIG. 2B, a flat bottom 34 of filter canister 10 is depicted resting on a flat upper surface 36 of vortex-mixing unit 32 while an engagement component, a rubber ring 40, of vortex-mixing unit 32 encircles the bottom of filter canister 10. When vortex-mixing unit 32 is activated, vortex-stirring inducing motion is transferred to filter canister 10, inter alia, by the engagement component, rubber ring 40. In FIG. 2B, rubber ring 40 constituting an engagement component completely encircles the entire bottom of filter canister 10. In some similar embodiments, the engagement component encircles only a portion of the bottom of a filter canister, e.g., is an incomplete ring. In some similar embodiments, the engagement component is made of a material different from rubber, e.g., plastic, silicone or metal.

In FIG. 2C, a non-flat (conical) bottom 42 of filter canister 10 is depicted resting on a non-flat upper surface 44 of vortex-mixing unit 32. Non-flat upper surface 44 of vortex-mixing unit 32 on which filter canister 10 rests and which encircles the bottom portion of filter canister 10, constitutes an engagement component of vortex-mixing unit 32. When vortex-mixing unit 32 of the device depicted in FIG. 2C is activated, vortex-stirring inducing motion is transferred to filter canister 10, inter alia, through the engagement component, non-flat upper surface 44. Some such embodiments having a non-flat bottom as an engagement component have an additional engagement component, for example the embodiment depicted in FIG. 2C also has a rubber ring 40 as an additional engagement component. Some embodiments similar to the depicted in FIG. 2C have a non-flat bottom as an exclusive engagement component.

In FIG. 2D, a flat bottom 34 of filter canister 10 is depicted resting on the smooth surface of a flat supporting shelf 46. The engagement component of vortex-mixing unit 32 depicted in FIG. 2D is a rubber-lined ring 48 which encircles the sides of filter canister 10. When vortex-mixing unit 32 is activated, vortex-stirring inducing motion is transferred to filter canister 10 through the sides thereof by the engagement component, rubber-lined ring 48. In FIG. 2D, rubber-lined ring 18 constituting an engagement component completely encircles the sides of filter canister 10. In some similar embodiments, the engagement component encircles only a portion of a filter canister, e.g., is an incomplete ring. In some similar embodiments, the engagement component is made of a material different from a rubber-lined ring, e.g., a ring lined with plastic, silicone or metal or an unlined ring made of plastic, rubber, silicone or metal.

Since the mechanical processing such as vortex-mixing is performed in a liposuction filter canister, the processing of the lipoaspirate, depending on the embodiment, is performed concurrently with the actual harvesting and/or very soon after the actual harvesting is completed under aseptic conditions as there is no need to transfer the lipoaspirate from the filter canister for processing. It is believed that mechanically-processing the lipoaspirate concurrently with the harvesting and/or soon after harvesting thereof is advantageous: without wishing to be held to any one theory, it is currently hypothesized that quick processing leads to less stress on the harvested adipose tissue. Accordingly, in some embodiments the mechanical processing is started within 60 minutes of the harvesting of the lipoaspirate. In some embodiments, the mechanical processing is performed within 45 minutes, within 30 minutes, within 15 minutes within 10 minutes, within 5 minutes, within 1 minute, within 30 seconds within 5 seconds and even concurrently with the harvesting of the lipoaspirate.

In some embodiments, the mechanical processing such as vortex-mixing is applied to the lipoaspirate with no additional material added into the liposuction filter canister. In some alternative embodiments, a volume of aqueous solution is added (e.g., through an access port 20 or other suitable component) to the liposuction filter canister prior and/or during application of the mechanical processing. It has been found that, in some embodiments (such as some embodiments of vortex mixing), the addition of an aqueous solution increases the efficacy of the mechanical processing, improving the results thereof. In such embodiments, the aqueous solution is preferably sterile. In some such embodiments, the aqueous solution is isotonic. Examples of suitable aqueous solutions include PBS (phosphate-buffered solution), saline and Ringer's solution. If added, the amount of aqueous solution is any suitable amount and in some embodiments is not more than 100%, not more than 80%, not more than 60% and even not more than 50% of the volume of lipoaspirate contained in the filter canister. In some embodiments, the amount of aqueous solution added is at least partially dependent on the characteristics of the container of the filter canister: the amount of aqueous solution added is such that not less than about 30%, not less than about 50% and even not less than about 65% of the lipoaspirate is below the level of the aqueous solution added to the filter canister. In preferred such embodiments, during the draining 'c', added aqueous solution is also drained from the liposuction filter canister.

Parameters of the Mechanical Processing

The parameters of the mechanical processing are any suitable parameters that achieve the desired effect. It is desirable that the mechanical processing be intensive enough to cause the pieces of lipid tissue in the lipoaspirate to fall apart sufficiently to release a substantial amount of beneficial factors from the tissue, but not so intensively that substantial amounts of harmful factors are released and/or that a substantial number of lipocytes are damaged.

In some embodiments vortex-mixing is performed at not more than 3000 rpm. In some embodiments, vortex-mixing is performed at not more than 1000 rpm, not more than 800 rpm and even not more than 700 rpm. That said, in some embodiments vortex-mixing is performed at not less than 60 rpm and even not less than 100 rpm.

Generally speaking, the duration of vortex-mixing is preferably as short as possible to save time, thereby making efficient use of the devices used for processing the lipoaspirate but sufficiently long so that a substantial amount of beneficial factors are released from the tissue. In some embodiments, vortex-mixing is performed for not more than 30 minutes, not more than 20 minutes, not more than 10 minutes and even not more than 7 minutes. In some embodiments, vortex-mixing is performed for not less than 30 seconds and even not less than 60 seconds.

Draining of Released Fluid

In 'c', subsequent to the mechanical processing, fluid released from the lipoaspirate as a result of the mechanical processing is removed from the liposuction filter canister. The released fluid contains harmful factors released from the lipoaspirate by the mechanical processing as well as remnants of blood and/or tumescent solution and, if present, any aqueous solution added to assist in the mechanical processing. Importantly, what remains trapped in the filter liner (22 in FIG. 1) is clean adipose tissue suitable for AFT that is somewhat enriched with beneficial factors. Although not wishing to be held to any one theory, it is currently hypothesized that the mechanical processing such as vortex-mixing gently breaks apart pieces of adipose tissue held in the filter canister, releasing beneficial factors that are ordinarily considered components of an SVF. Further, the mechanical processing such as vortex-mixing is apparently sufficiently gentle that it leads to the production and/or release of fewer harmful factors than is released during known methods of processing lipoaspirate. The mechanical processing such as vortex-mixing is also effective in removing at least some of the harmful factors (whether previously present or released as a result of the mechanical processing) that have passed through the filter liner.

In some embodiments, for draining the released fluid, the filter canister is detached from the liposuction vacuum module (22 in FIG. 2A) of the liposuction device and the filter canister containing the lipoaspirate is moved to another location for mechanical processing and/or for draining the released fluid. For example, in some embodiments, the filter canister is detached from the liposuction vacuum module of the liposuction device and is moved to a desired mechanical processing device for mechanical processing, for example, to a vortex mixer for vortex-mixing. In such embodiments, any suitable device and mechanism may be used for mechanically processing the lipoaspirate in the filter canister, in some embodiments, devices and/or mechanisms analogous to those depicted in FIGS. 2A-2D, 3A-3C and 4A-4H.

In some such embodiments, during the mechanical processing such as vortex-mixing, the filter canister is not attached (i.e., "attached" being an adjective) to a fluid drainage mechanism such as the liposuction vacuum module of the liposuction device. In such embodiments, subsequently to the mechanical processing, the filter canister containing the lipoaspirate is reattached to a fluid drainage mechanism to drain the fluid released from the lipoaspirate, for example, is reattached to the liposuction vacuum module of the liposuction device.

In preferred embodiments, the liposuction filter canister is attached (i.e., "attached" being an adjective) to a fluid drainage mechanism during the mechanical processing. In some such embodiments, during the mechanical processing, the filter canister is attached to a fluid drainage mechanism that is not the liposuction vacuum module of the liposuction device. In preferred embodiments, the filter canister remains connected to the liposuction vacuum module of the liposuction device to serve as the fluid drainage mechanism. In such embodiments, draining the fluid released from the lipoaspirate as a result of the mechanical processing is preferably performed by activating the liposuction vacuum module.

AFT with the Mechanically Processed Adipose Tissue

In some embodiments, the method further comprises subsequent to the draining 'c', transferring the lipoaspirate from the filter canister to an autologous fat transfer (AFT) device. An AFT device is any device or component of a device that is used for transplanting fat to a living subject, e.g., a syringe or a syringe barrel. In some embodiments, lipoaspirate is transferred directly, that is to say, from the filter canister to the AFT device. In some embodiments, lipoaspirate is transferred indirectly, e.g., from the filter canister to a container and from the container to the AFT device. For example, in some embodiments, a syringe 56 (as an AFT device such as a fat transplantation device or a container) is inserted through open access port 20 to remove the vortex-mixed adipose tissue.

In some embodiments, the method further comprises transplanting the lipoaspirate to a living subject using the AFT device, preferably to the same subject from whom the adipose tissue was harvested (autologously). In some embodiments, transplanting the lipoaspirate to a living subject is not part of the claimed invention.

Washing of the Mechanically Processed Adipose Tissue

As noted above, as a consequence of the mechanical processing, a fluid is released from the lipoaspirate and passes through the filter liner (22 in FIG. 1) to gather in the container (12 in FIG. 1) of the filter canister 10. The released fluid contains harmful materials released from the lipoaspirate as a result of the mechanical processing as well as remnants of blood and/or tumescent solution.

In some embodiments, subsequent to the mechanical processing of the lipoaspirate 'b' and preferably also subsequent to the draining of fluid 'c' (if done) but prior to the transferring of the vortex-mixed lipoaspirate to an AFT device, the method further comprises washing the mechanically-processed lipoaspirate by adding a washing solution (e.g., saline, Ringer's solution, PBS) to the filter canister and draining from the container in the usual way, e.g., by activating a fluid drainage mechanism such as the liposuction vacuum module or, in some embodiments, a separate drainage module. Such washing helps remove at least some of the harmful materials from the lipoaspirate. Such a washing solution is preferably sterile and/or isotonic.

In some preferred embodiments, subsequent to the mechanical processing of the lipoaspirate 'b' and preferably also subsequent to the draining of fluid 'c' (if done) but prior to the transferring of the mechanically-processed lipoaspirate to an AFT device, the mechanically-processed lipoaspirate in the liposuction filter canister is not washed. Additionally or alternatively, in some preferred embodiments, subsequent to the mechanical-processing of the lipoaspirate 'b' and preferably also subsequent to the draining of fluid 'c' (if done) but prior to the transferring of the mechanically-processed lipoaspirate to an AFT device, the mechanically-processed lipoaspirate in the liposuction filter canister is not centrifuged. Not having a washing step and/or a centrifugation step has numerous advantages including saving time and cost, inter alia by simplifying the device that is used for processing the lipoaspirate, obviating the need for providing a washing solution and reducing the amount of biological waste that needs to be disposed of. Surprisingly, embodiments of AFT performed using not-washed/not-centrifuged lipoaspirate that is mechanically-processed in accordance with the teachings herein are highly successful. This success indicates that the mechanical-processing releases sufficient beneficial materials that remain in the lipoaspirate to enrich the lipoaspirate. In parallel, sufficient harmful materials are removed from the lipoaspirate through the filter of the liposuction filter canister so as not to substantially reduce the quality of the lipoaspirate for AFT.

Capacity of Filter Canister and Volume of Lipoaspirate Processed

A person having ordinary skill in the art is aware that in the accepted prior art methods of processing lipoaspirate, improved AFT is necessarily performed only with low volumes of enriched adipose tissue, around 100 ml. This is a result of the complexity of producing an SVF for enriching the adipose tissue including vigorous mechanical and/or enzymatic processing of a portion of the lipoaspirate, followed by centrifugation to produce a 1-gram SVF pellet. The produced SVF pellet is then washed and subsequently added to a relatively small volume of adipose tissue (typically around 100 ml) that is thereby enriched and used for improved AFT.

According to the teachings herein, any desired volume of lipoaspirate contained inside the liposuction filter canister is processed by application of mechanical processing such as vortex-mixing to produce enriched lipoaspirate, limited only by the volume of the liposuction filter canister and by the amount of adipose tissue harvested from the subject.

Accordingly, in some embodiments, the liposuction filter canister containing the lipoaspirate has a volume of not less than 50 ml and not more than 10 liter and even not more than 5 liter. In some embodiments, the liposuction filter canister is selected from the group consisting of small-sized having a volume of not less than 50 ml and not more than 100 ml, medium-sized having a volume of not less than 100 ml and not more than 500 ml, large-sized having a volume of not less than 500 ml and not more than 1 liter and very large-sized having a volume of not less than 1 liter.

In some embodiments the amount of received harvested lipoaspirate contained in the liposuction filter canister is not less than 50 ml and not more than 10 liter. In some embodiments the amount of received harvested lipoaspirate contained in the liposuction filter canister is selected from the group consisting of not less than 50 ml and not more than 100 ml, not less than 100 ml and not more than 500 ml, not less than 500 ml and not more than 1 liter and even not less than 1 liter.

Enzymatic Processing

As discussed in the introduction, it is known to process lipoaspirate by addition of external enzymes to release stem cells and the like from the adipose tissue. In preferred embodiments of the teachings herein, no external enzyme is added to the lipoaspirate from the time of the harvesting through the draining of the fluid released from the lipoaspirate 'c' and, if applicable, through the transferring of the lipoaspirate to an AFT device. In some such preferred embodiments the lipoaspirate is devoid of contact with any external enzyme from prior to 'a' through immediately subsequent to 'b' and prior to 'c'. In some such preferred embodiments the lipoaspirate is devoid of contact with any external enzyme from prior to 'a' through immediately subsequent to 'c'. In some such preferred embodiments the lipoaspirate is devoid of contact with any external enzyme as long as the lipoaspirate is contained in the liposuction filter canister.

Liposuction

The teachings of the method herein are based on the discovery that gentle mechanical processing of harvested lipoaspirate allows for processing harvested lipoaspirate in a liposuction filter canister, yielding an enriched lipoaspirate for improved AFT.

It is currently believed that the processing method according to the teachings herein is exceptionally suitable for use together with high-quality lipoaspirate, that is to say, lipoaspirate that was harvested gently with relatively less trauma which results in less waste material such as blood, fewer dead or damaged lipocytes (also called adipocytes) and fewer traumatized lipocytes. Without being held to any one theory, it is believed that such a gently-harvested lipoaspirate includes fewer harmful factors. Accordingly, in some embodiments, the received lipoaspirate is lipoaspirate harvested using a gentle liposuction method and/or device.

In some embodiments, the gentle liposuction method is ultrasound-assisted liposuction and liposuction was performed using an ultrasound-assisted liposuction device.

In some embodiments, the gentle liposuction method is radio frequency (RF)-assisted liposuction and liposuction was performed using an RF-assisted liposuction device.

In some embodiments, the lipoaspirate was harvested using a cannula with an internal diameter of at least 2 mm and not more than 5 mm.

In some embodiments, the lipoaspirate was harvested using a suction pressure of at least 20 kP and not more than 98 kP.

In some embodiments of the method, the received lipoaspirate is harvested from a subject using laser-assisted liposuction using a laser-assisted liposuction device, as depicted in FIGS. 2A-2D. In some such embodiments, the laser-assisted liposuction is performed using a laser wavelength within the range of 800-1600 nm, 1400-1500 nm, 1450-1490 nm and even 1460-1480 nm, for example a laser wavelength of 1470 nm as is used in some commercially-available laser-assisted liposuction devices such as LipoLife® by Alma Lasers (Caesarea, Israel). In some such embodiments, the laser-assisted liposuction is performed using a radially-irradiating optical fiber as is used in some commercially-available laser-assisted liposuction devices such as LipoLife® by Alma Lasers.

Without wishing to be held to any one theory, it is currently believed that laser-assisted liposuction, especially using the above-recited wavelengths and/or a radially-irradiating optical fiber, is very gentle and produces fewer harmful factors than other liposuction methods.

Additional Processing of the Lipoaspirate

As noted above, subsequent to the mechanical processing 'b' or the draining of released fluid 'c', the processed lipoaspirate inside the liposuction filter canister is typically ready for use in AFT, with or without a subsequent washing step.

That said, in some instances, subsequent to 'c' the processed lipoaspirate is insufficiently fluid for some types of AFT, typically indicating that the processed lipoaspirate includes a relatively large proportion of relatively large pieces of adipose tissue. Further, in some instances it is desired to additionally or alternatively produce an SVF for use, either to enrich lipoaspirate for AFT or for other therapeutic purposes.

It has been found by the Inventors that it is possible to further process the lipoaspirate contained in the liposuction filter canister subsequent to draining 'c', yielding a more fluid lipoaspirate that is suitable for AFT and/or an SVF. Thus, in some embodiments the method further comprises:

d. subsequent to 'c', applying additional mechanical processing such as vortex-mixing to the lipoaspirate contained in the liposuction filter canister to mix the lipoaspirate, the additional mechanical processing reducing the average size of adipose tissue pieces in the lipoaspirate without substantially rupturing lipocytes therein.

The parameters of the additional mechanical processing (including: time subsequent to harvesting, addition or no addition of additional material to the liposuction filter canister, the intensity at which the mechanical processing is performed, the duration the mechanical processing is performed) are as described above for the vortex-mixing of 'b' (and herein for other mechanical processing methods) and, for reasons of brevity, not recited again.

In some embodiments, the additional mechanical processing 'd' is performed subsequent to 'c' on the entire contents of the liposuction filter canister. In some alternate embodiments, subsequent to 'c' some of the lipoaspirate is removed from the liposuction filter canister and the additional mechanical processing is performed only on the lipoaspirate remaining in the liposuction filter canister. In some embodiments, the type of mechanical processing in 'b' is different from the type of mechanical processing in 'd'. For simplicity, in preferred embodiments the type of mechanical processing in 'b' is the same as the type of mechanical processing in 'd'.

Fluid Lipoaspirate

It has been found that subsequent to 'd', the additional mechanical processing of the lipoaspirate renders the lipoaspirate more fluid and therefore suitable, in some embodiments, for AFT in finer regions of the body or for finer definition of the body. It is currently believed that the additional mechanical processing reduces the average size of the pieces of adipose tissue making up the lipoaspirate. It is also believed that additional beneficial factors are released while relatively few harmful factors are released, so that the lipoaspirate is considered enriched for use in improved AFT.

Accordingly, in some embodiments, the method further comprises: subsequent to the additional mechanical processing 'd', transferring the lipoaspirate to an autologous fat transfer (AFT) device. In some embodiments, lipoaspirate is transferred directly, that is to say, from the filter canister to the AFT device. In some embodiments, lipoaspirate is transferred indirectly, e.g., from the filter canister to a container and from the container to the AFT device. In some embodiments, the method further comprises transplanting the liposuction to a living subject using the AFT device, preferably to the same subject from which the adipose tissue was harvested (i.e., autologously).

Stromal Vascular Factor

As with the first mechanical processing 'b', the additional mechanical processing 'd' releases a fluid that passes through the filter liner of the liposuction filter canister. It has been found that this fluid is enriched with beneficial factors such as stem cells which can be gathered and concentrated in the usual way to make an SVF pellet.

Accordingly, in some embodiments the method further comprises:

e. subsequent to the additional mechanical processing 'd', isolating fluid released from the lipoaspirate consequent to the additional mechanical processing as an SVF fluid.

In some embodiments, the SVF fluid is processed to make an SVF pellet. In some such embodiments, such processing includes placing the SVF fluid in a centrifugation vessel and centrifuging the SVF fluid in the centrifugation vessel to yield an SVF pellet at the bottom of the centrifugation vessel. The SVF pellet can be used in the usual way, for example, is suspended in a fluid as an injectable therapeutic or is added to adipose tissue/lipoaspirate to enrich adipose tissue for AFT, including lipoaspirate processed in accordance with the teachings herein.

Device for Implementing the Method

Embodiments of the method according to the teachings herein can be performed using a suitable device or combination of devices, as discussed hereinabove. Some embodiments are preferably implemented using a liposuction device according to the teachings herein, such as device 24 discussed with reference to FIGS. 2A-2D above or the devices depicted in FIGS. 3A-3C or FIGS. 4A-4H. In some embodiments, such a liposuction device is substantially a liposuction device 24 configured for performing liposuction, the device comprising a vortex mixing unit as a lipoaspirate-processing unit (e.g., 32 depicted in FIGS. 2A-2D), the vortex-mixing unit configured, when activated, to produce and apply vortex-inducing motion at an intensity and for a duration to a liposuction filter canister functionally-associated with the liposuction device to implement one or more embodiments of the method according to the teachings herein. Such vortex-inducing motion induces the formation of a vortex in the contents of the liposuction filter canister, thereby vortex-mixing the contents of the liposuction filter canister.

As discussed above, embodiments of such a device can include one or more of:

a liposuction vacuum module, such as known in the art, to effect liposuction and in some embodiments that can function as a fluid drainage module to remove liquids from a liposuction filter canister such as fluids released from lipoaspirate as a result of the vortex-mixing;

a fluid drainage module that is different from the liposuction vacuum module to remove liquids from a liposuction filter canister such as fluids released from lipoaspirate as a result of the vortex-mixing;

a liposuction probe having a distal end attachable to a liposuction cannula and a proximal end attachable to a liposuction filter canister functionally-associated with the liposuction device through an aspirate inlet thereof, configured to direct liposuction aspirate harvested via a liposuction cannula from said distal end through said proximal end into a container of the attached liposuction filter canister;

a washing module attachable to a liposuction filter canister functionally-associated with the liposuction device through an access port thereof, configured to add an amount of liquid (e.g., washing solution) into a container of the attached liposuction filter canister (preferably a metered amount of liquid); and a controller configured to automatically process lipoaspirate (preferably in accordance with an embodiment of the method according to the teachings herein) contained in a liposuction filter canister functionally associated with the liposuction device, the automatic processing comprising activation of the vortex-mixing unit, the fluid drainage module (in some embodiments where the fluid drainage module is the same as the liposuction vacuum module and in other embodiments where the fluid drainage module is different from the liposuction vacuum module) and the washing module in a desired order, preferably in accordance with an embodiment of the teachings herein. A person having ordinary skill in the art is able to implement a controller with no inventive effort upon perusal of the description. Typically, the controller is implemented as series of commands to the modules (implemented in software, hardware and/or firmware) on a computer (custom or general purpose, e.g., the computer that also functions as a controller to operate the liposuction device to perform liposuction), communication devices and protocols to the various controlled modules and, in some embodiments, electrical and/or electromechanical components such as switches, solenoids and robotic arms.

Liposuction device 24 depicted in FIG. 2A includes a controller 50 and a washing module 52. Liposuction vacuum module 26 is configured also to function as a fluid drainage module.

Mechanical Processing by Vibration

As noted above, in some embodiments the method is implemented where the mechanical processing is vibration.

Similarly, in some embodiments, the lipoaspirate processing unit of a device according to the teachings herein comprises a vibration unit (instead of or in addition to a vortex-mixing unit), the vibration unit configured, when activated, to produce and apply vibrations to lipoaspirate contained inside a liposuction filter canister functionally-associated with the liposuction device, the vibrations effective to mechanically process the lipoaspirate.

The applied vibrations are of any suitable frequency and intensity to achieve the desired balance of mechanical processing without substantially rupturing lipocytes. A person having ordinary skill in the art is able to determine a suitable frequency and intensity to achieve the desired effect without undue experimentation.

It is known in the art that vibrations having ultrasonic frequencies higher than 20 kHz cause in vitro cell lysis. Accordingly, in some embodiments the applied vibrations have a frequency of less than 20 kHz, less than 10 kHz and even less than 5 kHz. Suitable devices for generating suitable frequencies include commercially-available low-frequency sonic transducers, e.g., from Sensor Technology Ltd. (Collingwood, Ontario, Canada).

In some embodiments, the vibration unit and/or a controller of the liposuction device are configured to allow vibration of the contents of a liposuction filter canister functionally-associated with the liposuction device for a period of not more than 30 minutes, not more than 20 minutes, not more than 10 minutes and even not more than 7 minutes.

In some embodiments, the vibration unit and/or the controller are configured to allow vibration of the contents of a liposuction filter canister functionally-associated with the liposuction device for a period of not less than 30 seconds and even not less than 60 seconds.

Figure 3B:
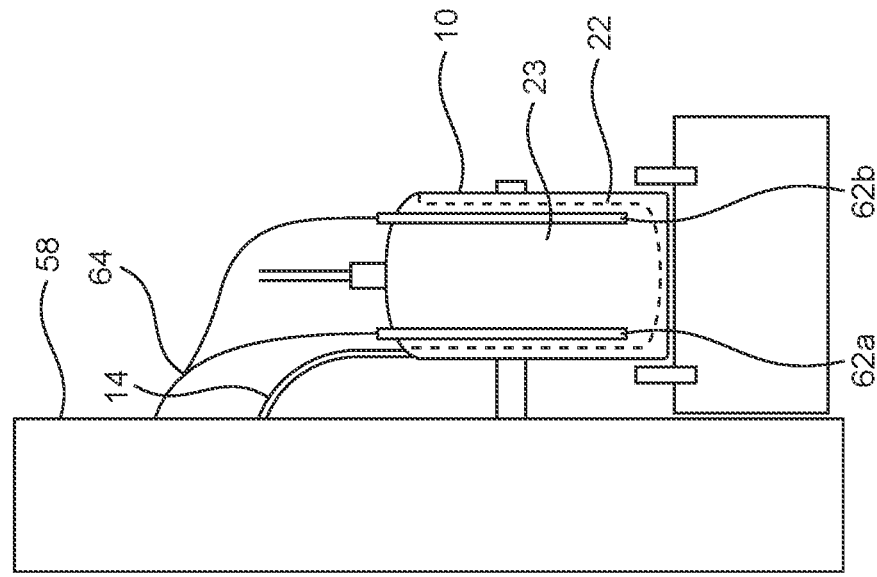
FIGS. 3A-3C are schematic depictions of components of embodiments of devices useful for implementing embodiments of the methods according to the teachings herein, the devices including a vibration unit.
Figure 3A:
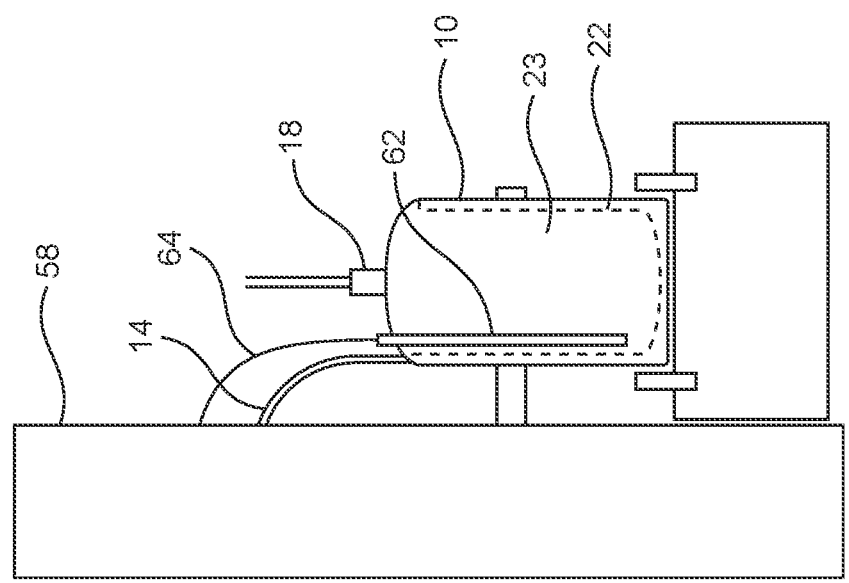
Figure 3C:
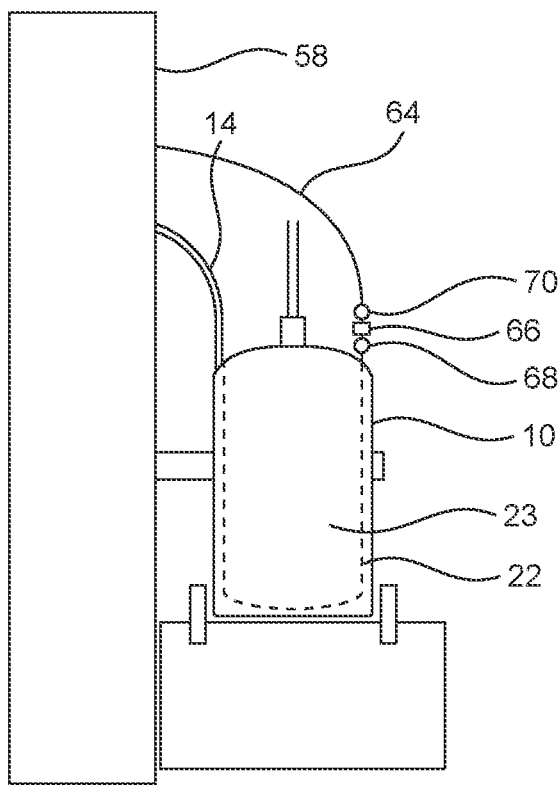

FIGS. 3A-3C are schematic depictions of components of embodiments of devices useful for implementing embodiments of the methods according to the teachings herein where the mechanical processing is vibration, liposuction devices 58 including a vibration unit 60 as a lipoaspirate processing unit.

Sonic Transmitter Probe

In some embodiments, the vibration unit comprises at least one sonic transmitter probe configured to be positioned inside a volume enclosed by a filter liner of a liposuction filter canister functionally-associated with the liposuction device. As is known in the art of sonic treatment, a sonic transmitter probe is a device that produces vibrations and transfers the vibrations to a medium, e.g., the lipoaspirate according to the teachings herein. In such embodiments, during use the probe is at least partially immersed in the lipoaspirate.

In some embodiments, the vibration unit comprises a single sonic transmitter probe. An advantage of single transmitter probe is simplicity. In FIG. 3A is depicted a filter canister 10 in cross section, functionally associated with a device 58. Positioned inside inner volume 23 of canister 10 is an elongated sonic transmitter probe 62 so that when volume 23 contains a fluid such as lipoaspirate, probe 62 is immersed therein. Sonic transmitter probe 62 is functionally associated with the controller (not depicted) of device 58 through cable 64. When required, the controller provides the required power for the required duration so that probe 62 produces vibrations for processing lipoaspirate contained in volume 23 in accordance with the teachings herein.

In some embodiments, the vibration comprises at least two, at least three and even at least four sonic transmitter probes. An advantage of two or more sonic probes is that the mechanical processing caused by the vibration of the probes is more effectively distributed in the entire volume of the lipoaspirate. In some embodiments, one or more of the sonic transmitter probes are elongated. In FIG. 3B is depicted a filter canister 10 functionally associated with a device 58. Device 58 depicted in FIG. 3B is the same as depicted in FIG. 3A but includes two elongated sonic transmitter probes 62a and 62b.

In some such embodiments, some or all of a sonic transmitter probe is a component of a liposuction filter canister and the liposuction device is configured, for example includes electrical connectors, to allow operation of the sonic transmitter probe of the liposuction canister in accordance with the teachings herein. Alternatively or additionally, in some embodiments, some or all of a sonic transmitter probe is a component of the liposuction device.

In some embodiments, the probe is covered with a cover such as sheath for use to prevent non-sterile contact of the probe with lipoaspirate. In some embodiments, at least the outer portion of the probe is disposed after use.

Vibrating Filter Liner

In some embodiments, the vibration unit comprises a sonic transmitter configured to physically-associated with a filter liner of a liposuction filter canister functionally-associated with the liposuction device so that when activated, said sonic transmitter causes a physically-associated filter liner to vibrate. In such embodiments, the vibrating filter liner transfers the vibrations from the sonic transmitter to the lipoaspirate held therein. In such embodiments, at least part of the filter liner is made of a material that transfers sonic vibrations such as a medical grade metal or a medical grade plastic such as polyester. In some such embodiments, the sonic transmitter is a component of a liposuction filter canister and the liposuction device is configured, for example includes electrical connectors, to allow operation of the sonic transmitter of the liposuction canister in accordance with the teachings herein. Alternately, in some such embodiments, the sonic transmitter is a component of the device and the liposuction filter canister is a separate component, where the two are configured to allow reversible sonic mating of the transmitter with the filter liner.

In FIG. 3C is depicted a filter canister 10 functionally associated with a device 58. Functionally associated with filter liner 22 of canister 10 is a sonic transmitter 66 functionally associated with the controller (not depicted) of device 58 through cable 64. When required, the controller provides the required power for the required duration so that transmitter 66 produces vibrations that are transferred by filter liner 22 to lipoaspirate contained in volume 23 to process the lipoaspirate.

In some embodiments, sonic transmitter 66 is a component of device 58 that is reversibly coupled with filter liner 22 through a connector 68.

In some alternate embodiments, sonic transmitter 66 is a component of canister 10 that is reversibly coupled with device 58 through cable 64 through a connector 70.

Mechanical Mixing.

As noted above, in some embodiments the method is implemented where the mechanical processing is mechanical mixing.

Similarly, in some embodiments, the lipoaspirate processing unit of a device according to the teachings herein comprises:

a mechanical mixing component configured to be positioned inside a volume enclosed by a filter liner of a liposuction filter canister functionally-associated with the liposuction device; and a mixing motor configured to move lipoaspirate contained in the volume relative to the mechanical mixing component to mechanically-mix the lipoaspirate, the mechanical mixing effective to mechanically process the lipoaspirate.

FIGS. 4A-4H are schematic depictions of components of embodiments of devices useful for implementing embodiments of the methods according to the teachings herein, the devices configured for mechanical mixing.

Translation Mixing Component

In some embodiments, a mixing motor is configured so that the relative motion of the mechanical mixing component to the liposuction filter canister is translation in parallel to the longitudinal axis of the liposuction filter canister. In some embodiments, the filter canister is moved in parallel to the longitudinal axis. Additionally or alternatively, in some embodiments, the mechanical mixing component is moved in parallel to the longitudinal axis.

In some such embodiments, the mixing component is a flow-restricting barrier, that is to say, the mixing component constitutes a partial barrier to flow of lipoaspirate therethrough. As a result of the translation of the canister relative the mixing component, lipoaspirate contained in the inner volume of the filter liner passes through and/or alongside the mixing component (between the mixing component and the filter liner) in a restricted, increased-pressure, flow which leads to mechanical mixing of the lipoaspirate that is effective to mechanically-process the lipoaspirate.

In some such embodiments, the flow-restricting barrier comprises or is a partially-pervious plunger. As used herein, a partially-pervious plunger is a flow-restricting barrier having a small dimension parallel to the longitudinal axis and a larger dimension perpendicular to the longitudinal axis which is partially-pervious, that is to say, configured to allow lipoaspirate contained in the inner volume of the filter liner to pass through the plunger or alongside the plunger (between the plunger and the filter liner itself). A partially-pervious plunger is contrasted with an impervious plunger, a component of prior art syringes that does not allow a fluid to pass therethrough or alongside.

Figures 1, 4A:
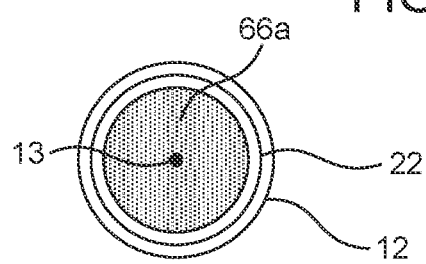

In some embodiments, the outline of a partially-pervious plunger in the dimension perpendicular to the longitudinal axis 13 is round, e.g., plunger 66a in cross-section from above in FIG. 4A-1, a solid thin plate that has a diameter smaller than the inner diameter of liner 22 so that during translation lipoaspirate passes in the space between the rim of plunger 66a and the inner wall of liner 22.

Figures 2, 4A:
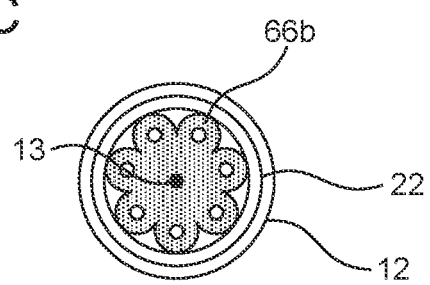

In some embodiments, the outline of the plunger in the dimension perpendicular to the longitudinal axis 13 is indented, e.g., flower-shaped plunger 66b in cross-section from above in FIG. 4A-2, a perforated flower-shaped plate so that during translation lipoaspirate passes in the space between the indentations and through the perforations.

In some embodiments, the outline of the plunger in the dimension perpendicular to the longitudinal axis 13 is the same as the profile of the inner wall of the liner such as plunger 66a in FIG. 4A-1.

Figures 3, 4A:
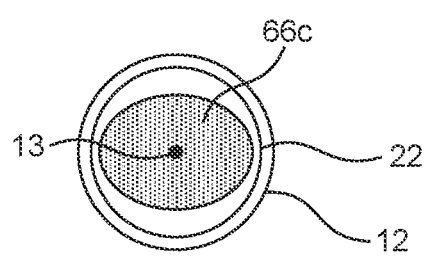

In some embodiments, the outline of the plunger in the dimension perpendicular to the longitudinal axis 13 is different from the profile of the inner wall of the liner such as plunger 66b in FIG. 4A-1 or plunger 66c in cross section from above in FIG. 4A-3.

In some embodiments, the plunger is devoid of gaps that allow passage of lipoaspirate therethrough such as plunger 66a in FIG. 4A-1 or 66c in FIG. 4A-3.

Figures 4, 4A:
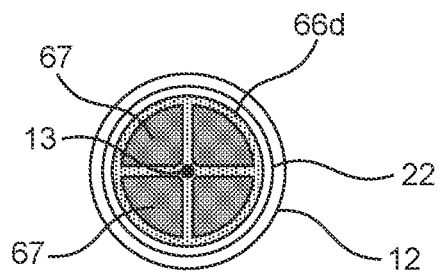

In some embodiments, the plunger is perforated such as perforated plunger 66b in FIG. 4A-2 or mesh plunger 66d in FIG. 4A-4 where lipoaspirate can pass through the mesh 67 that constitutes portions of plunger 66d in a manner analogous to a French press.

The speed of the relative translational motion is any suitable speed and is typically dependent on the characteristics of the mixing component: e.g., more restrictive barriers are moved more slowly while less restrictive barriers are moved more quickly. In some preferred embodiments, the speed is between 1 mm/sec to 10 cm/sec. In some embodiments, the device (e.g., the controller) is configured so that the movement is performed only once in one direction (e.g., from top to bottom or from bottom to top). In some alternate embodiments, the movement is performed at least twice (e.g., from top to bottom and back to the top, or from bottom to top and back to the bottom).

In FIG. 4B is depicted a liposuction device 68 functionally-associated with a filter canister 10. Inside an inner volume 23 defined by filter liner 22 is a mechanical mixing component, comprising a pervious plunger 66 and rigid straight support bar 70 parallel with longitudinal axis 13 and fixed to device 68. A mixing motor 72 is configured to move filter canister 10 in parallel to axis 13 while partially-pervious plunger 66 and bar 70 do not move so that lipoaspirate in volume 23 is forced past and/or through plunger 66 to be mixed and thereby mechanically processed.

In FIG. 4C is depicted a liposuction device 74 similar to device 68. In device 74, filter canister 10 is fixed in place relative to device 74 and mixing motor 72 is configured to move partially-pervious plunger 66 and rigid straight support bar 70 parallel with longitudinal axis 13.

Rotating Filter Liner Mixing Component

Alternately or additionally to translation mixing, in some embodiments, a mixing motor is configured to rotate the filter liner relative to a container of the liposuction filter canister around an axis parallel to the longitudinal axis of the liposuction canister. In some such embodiments, the mechanical mixing component comprises mixing elements protruding from an inner surface of the filter liner into the inner volume, the mixing elements rotating together with the filter liner. Additionally or alternately, in some embodiments the mechanical mixing component comprises mixing elements that do not rotate together with the filter liner.

In FIG. 4D is depicted a liposuction device 76 functionally-associated with a filter canister 10, filter canister 10 depicted in schematic cross-section. Electrical mixing motor 72 is configured when activated to rotate filter liner 22 via a gear 78 that engages matching gear teeth 80 in the upper inner rim of filter liner 22. Protruding from an inner surface of filter liner 22 into inner volume 23 are mixing elements 82, 3 mm thick rigid polyethylene paddles. When mixing motor 72 is activated, filter liner 22 and mixing elements 82 rotate together around axis 13, mixing and thereby mechanically processing lipoaspirate contained in volume 23.

In FIG. 4E is depicted a liposuction device 84 similar to device 76. Inside inner volume 23 and fixedly mounted to the cap of filter canister 10 are stator paddles 86 (of 3 mm thick polyethylene. Operation of mixing motor 72 of device 84 is similar to that of device 76, but the presence of stator paddles 86 increases the efficiency of the mechanical processing of the lipoaspirate.

Rotating Mixing Component

Alternately or additionally to translation mixing and/or a rotating filter liner, in some embodiments a mixing motor is configured to rotate a mechanical mixing component separate from the filter liner that is located inside the inner volume of the filter liner, typically but not necessarily the rotation in a plane perpendicular to the longitudinal axis of the liposuction filter canister.

Any suitable type or combination of types of mechanical mixing component separate from the filter liner may be used.

In some embodiments, the mechanical mixing component comprises an impeller. In some embodiments, the impeller is a radial-flow impeller. Alternatively, in some embodiments the impeller is an axial-flow impeller. In FIG. 4F is depicted a liposuction device 88 functionally-associated with a filter canister 10, filter canister 10 depicted in schematic side cross-section. Electrical mixing motor 72 is configured when activated to rotate an impeller 90 through axle 92, mixing and thereby mechanically processing lipoaspirate contained in volume 23.

Alternately or additionally, in some embodiments the mechanical mixing component comprises a propellor, a mechanical mixing component that drives a fluid such as lipoaspirate contained in inner volume 23 axially. In FIG. 4G is depicted a liposuction device 94 functionally-associated with a filter canister 10, filter canister 10 depicted in schematic side cross-section. Electrical mixing motor 72 is configured when activated to rotate a propeller 96 through axle 92, mixing and thereby mechanically processing lipoaspirate contained in volume 23.

Figure 4H:
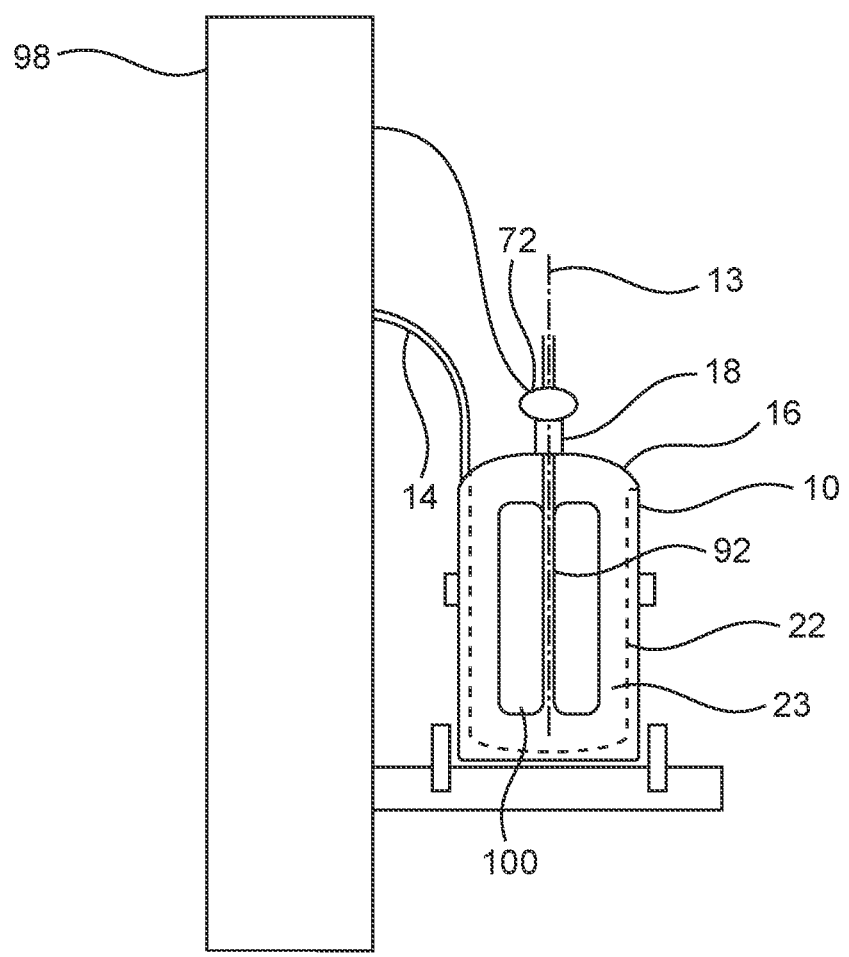

Alternately or additionally, in some embodiments the mechanical mixing component comprises a paddle, a mechanical mixing component having a flat surface that drives a fluid such as lipoaspirate contained in inner volume 23 tangentially to the rotation axis. In FIG. 4H is depicted a liposuction device 98 functionally-associated with a filter canister 10, filter canister 10 depicted in schematic side cross-section. Electrical mixing motor 72 is configured when activated to rotate a paddle 100 (of 3 mm thick polyethylene) through axle 92, mixing and thereby mechanically processing lipoaspirate contained in volume 23.

In embodiments having a mechanical mixing component (e.g., a rotating filter liner and or rotating mixing component separate from the filter liner), the rate and duration at which the mechanical mixing component is rotated is any suitable rate. In some embodiments, the mechanical mixing unit and/or a controller are configured to allow mechanical-mixing of the contents of a liposuction filter canister functionally-associated with the liposuction device for a period of not more than 10 minutes, not more than 5 minutes, not more than 1 minutes and even not more than 1 minute. Additionally, in some embodiments, the mechanical-mixing unit and/or the controller are configured to allow mechanical-mixing of the contents of a liposuction filter canister functionally-associated with the liposuction device for a period of not less than 10 seconds and even not less than 15 seconds. In some preferred embodiments, the rate of rotation of the mechanical mixing component is less than 960 rpm, less than 480 rpm, less than 240 rpm and even less than 120 rpm.

In some such embodiments, the mixing motor and the entire mechanical mixing component (e.g., plunger and handle) are components of the liposuction device.

In some such embodiments, the mixing motor and part of the mechanical mixing component (e.g., handle) are components of the liposuction device and part of the mechanical mixing component (e.g., plunger) is part of the filter canister.

In some such embodiments, the mixing motor is a component of the liposuction device and the entire mechanical mixing component (e.g., plunger and handle) are components of the filter canister.

In some such embodiments, the mixing motor and the entire mechanical mixing component (e.g., plunger and handle) are components of the filter canister. In some such embodiments, the liposuction device provides power (e.g., electrical power) to operate the mixing motor. Alternatively, in some such embodiments power to operate the electrical motor is provided from a source different than the liposuction device.

In some embodiments, a liposuction device includes more than one type of mixing component.

The teachings herein can be advantageously be implemented using any type of liposuction and liposuction device, but are advantageously implemented using more gentle liposuction devices.

For example, in some embodiments, liposuction device 24 depicted in FIG. 2A is an ultrasound-assisted liposuction device and component 54 is an ultrasound module including some of the components required to apply ultrasound energy to adipose tissue undergoing liposuction.

For example, in some embodiments, liposuction device 24 depicted in FIG. 2A is a RF-assisted liposuction device and component 54 is a RF module including some of the components required to apply radiofrequency energy to adipose tissue undergoing liposuction.

For example, in some embodiments, liposuction device 24 depicted in FIG. 2A is a laser-assisted liposuction device and component 54 is a laser module including some of the components required to apply laser energy to adipose tissue undergoing liposuction. For example, in some embodiments, the liposuction device is a modified LipoLife® laser-assisted liposuction device by Alma Lasers.

Similarly, in some embodiments any one of liposuction devices 58 (FIGS. 3A-3C), device 68 depicted in FIG. 4B), device 74 depicted in FIG. 4C), device 76 depicted in FIG. 4D), device 84 depicted in FIG. 4E), device 88 (FIG. 4F), device 94 (FIG. 4G), or device 98 (FIG. 4H) are one of an ultrasound-assisted liposuction device, RF-assisted liposuction device or laser-assisted liposuction device.

Unless otherwise defined, all technical and scientific terms used herein have the same meaning as commonly understood by one of ordinary skill in the art to which the invention pertains. In case of conflict, the specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof.

As used herein, the indefinite articles "a" and "an" mean "at least one" or "one or more" unless the context clearly dictates otherwise.

As used herein, when a numerical value is preceded by the term "about", the term "about" is intended to indicate +/−10%.

As used herein, a phrase in the form "A and/or B" means a selection from the group consisting of (A), (B) or (A and B). As used herein, a phrase in the form "at least one of A, B and C" means a selection from the group consisting of (A), (B), (C), (A and B), (A and C), (B and C) or (A and B and C).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

What is claimed is:

1. A liposuction device configured for performing liposuction by drawing in vivo adipose tissue from a body as a lipoaspirate containing lipocytes through a cannula and transporting at least some the harvested adipose tissue into a liposuction filter canister functionally associated with the liposuction device, the liposuction device comprising:

a vortex mixing unit configured to produce a vortex-inducing motion and having an engagement component configured to couple the liposuction filter canister to the vortex mixing unit and to apply vortex-inducing motion to the liposuction filter canister, wherein the vortex-inducing motion applied to the liposuction filter canister reduces an average size of pieces of the lipoaspirate without substantially rupturing the lipocytes contained therein.

2. The liposuction device of claim 1, further comprising a liposuction vacuum module attachable to the liposuction filter canister through a vacuum port thereof, the liposuction vacuum module configured, when attached to the liposuction filter canister and activated, to effect liposuction through the liposuction filter canister and through a liposuction probe functionally associated therewith, thereby allowing trapping of consequently-harvested adipose tissue in a filter liner of the liposuction filter canister.

3. The liposuction device of claim 2, configured to vortex-mix contents of the liposuction filter canister while the liposuction filter canister is attached to the liposuction vacuum module.

4. The liposuction device of claim 2, the liposuction vacuum module further configured to function as a fluid drainage module to remove liquids from a container of the liposuction filter canister.

5. The liposuction device of claim 2, comprising a fluid drainage module different from the liposuction vacuum module, attachable to the liposuction filter canister through a drainage port thereof, said fluid drainage module configured, when attached to the liposuction filter canister and activated, to remove liquids from a container of the liposuction filter canister.

6. The liposuction device claim 1, further comprising a liposuction probe having a distal end attachable to a liposuction cannula and a proximal end attachable to the liposuction filter canister through an aspirate inlet thereof, configured to direct liposuction aspirate harvested via a liposuction cannula from said distal end through said proximal end into a container of the liposuction filter canister.

7. The liposuction device of claim 1, further comprising a washing module attachable to the liposuction filter canister through an access port thereof, configured to add a metered amount of liquid into a container of liposuction filter canister.

8. The liposuction device of claim 7, further comprising a controller configured to automatically process lipoaspirate contained in the liposuction that is functionally associated with the liposuction device, the automatic processing comprising activation of the vortex mixing unit, the fluid drainage module and the washing module in a desired order.

9. The liposuction device of claim 1, the vortex mixing unit configured so that a bottom of the filter canister rests on the vortex mixing unit.

10. The liposuction device of claim 1, the vortex mixing unit includes a flat upper surface on which a flat bottom of the filter canister rests.

11. The liposuction device of claim 10, the engagement component includes the flat upper surface.

12. The liposuction device of claim 10, wherein the engagement component at least partially encircles a bottom of the filter canister resting on the flat upper surface.

13. The liposuction device of claim 1, the vortex mixing unit includes a non-flat upper surface on which a non-flat bottom of the liposuction filter canister rests, the non-flat upper surface encircling at least part of a bottom portion of the filter canister.

14. The liposuction device of claim 1, wherein the engagement component is configured to at least partially encircle at least a portion of the liposuction filter canister.

15. The liposuction device of claim 1, the vortex mixing unit configured, when activated, to vortex-mix the contents of the liposuction filter canister at not more than 1000 rpm.

16. The liposuction device of claim 1, wherein the average size of the pieces of the lipoaspirate is reduced by 50%.

17. The liposuction device of claim 1, wherein the average size of the pieces of the lipoaspirate is reduced by 75%.

18. The liposuction device of claim 1, wherein at least 90% of the lipocytes are not ruptured.

19. The liposuction device of claim 1, wherein at least 95% of the lipocytes are not ruptured.

* * * * *